(12) United States Patent
Moon et al.

(10) Patent No.: US 10,808,018 B2
(45) Date of Patent: Oct. 20, 2020

(54) ERYTHROPOIETIN-DERIVED PEPTIDES AND METHODS OF PROTECTING CELLS FROM OXIDATIVE DAMAGE INDUCED BY REACTIVE OXYGEN SPECIES

(71) Applicant: SYLUS CO., LTD., Jeonju-si, Jeollabuk-do (KR)

(72) Inventors: Che il Moon, Daegu (KR); Seung Yoo, Gyeongsan-si (KR); Chang-Hun Lee, Daegu (KR); So Kim, Daegu (KR); Deok Lee, Ansan-si (KR)

(73) Assignee: SYLUS CO., LTD., Jeollabuk-Do (KR)

( * ) Notice: Subject to any disclaimer, the term of this patent is extended or adjusted under 35 U.S.C. 154(b) by 0 days.

(21) Appl. No.: 16/551,060

(22) Filed: Aug. 26, 2019

(65) Prior Publication Data

US 2019/0375810 A1 Dec. 12, 2019

Related U.S. Application Data

(63) Continuation of application No. PCT/KR2018/002396, filed on Feb. 27, 2018.

(30) Foreign Application Priority Data

Feb. 27, 2017 (KR) .................. 10-2017-0025370

(51) Int. Cl.
```
C07K 2/00      (2006.01)
C07K 4/00      (2006.01)
C07K 5/00      (2006.01)
C07K 7/00      (2006.01)
C07K 14/00     (2006.01)
C07K 14/475    (2006.01)
C07K 14/48     (2006.01)
A61K 38/18     (2006.01)
A61K 38/00     (2006.01)
A61K 49/00     (2006.01)
```
(Continued)

(52) U.S. Cl.
CPC ........ *C07K 14/505* (2013.01); *A61K 38/1816* (2013.01); *C07K 14/4702* (2013.01); *C12N 15/86* (2013.01); *A61K 38/00* (2013.01); *A61K 38/179* (2013.01); *A61K 38/1709* (2013.01); *A61K 47/64* (2017.08); *A61K 2039/55516* (2013.01); *A61K 2039/6031* (2013.01); *A61K 2300/00* (2013.01); *A61P 9/00* (2018.01); *A61P 9/10* (2018.01); *A61P 21/00* (2018.01); *A61P 25/00* (2018.01); *A61P 25/02* (2018.01); *A61P 25/28* (2018.01); *C07K 7/08* (2013.01); *C07K 14/435* (2013.01); *C07K 14/47* (2013.01); *C07K 14/4705* (2013.01); *C07K 14/71* (2013.01); *C07K 2319/00* (2013.01); *C07K 2319/70* (2013.01); *C12N 15/85* (2013.01); *C12P 21/02* (2013.01); *G01N 33/5005* (2013.01); *G01N 33/5044* (2013.01); *G01N 33/5058* (2013.01); *G01N 33/68* (2013.01); *G01N 2800/52* (2013.01)

(58) Field of Classification Search
CPC ...... A61K 38/00; A61K 38/17; A61K 38/177; A61K 38/1816; A61K 48/00; A61K 2300/00; A61K 2039/55516; A61K 2039/6031; A61K 47/64; A61K 38/179; C07K 2319/00; C07K 14/505; C07K 14/435; C07K 14/705; C07K 2319/70; C07K 14/47; C07K 14/4702; C07K 14/4705; C07K 7/08; C07K 14/71; G01N 33/5005; G01N 2800/52; G01N 33/5058; G01N 33/68; G01N 33/5044; C12P 21/02; C12N 15/85; A61P 9/10; A61P 25/00; A61P 29/00; A61P 9/00; A61P 21/00; A61P 25/28; A61P 25/02; Y02A 90/26
See application file for complete search history.

(56) References Cited

U.S. PATENT DOCUMENTS 8,329,652 B2 * 12/2012 Berezin ................ C07K 14/505
                                                    514/17.7
9,044,428 B2 *  6/2015 Berezin ................ C07K 14/505
(Continued)

FOREIGN PATENT DOCUMENTS

EP          3587443      *  2/2018
KR      10-1148191 B1       5/2012
(Continued)

OTHER PUBLICATIONS

Blight Nat. Neurosci. 2002. 5: 1051-4.*
(Continued)

*Primary Examiner* — Chang-Yu Wang
(74) *Attorney, Agent, or Firm* — Cantor Colburn LLP

(57) ABSTRACT

A peptide is described herein that has: (i) a simple structure compared to existing natural human erythropoietin, thus capable of easily passing through a tissue-blood barrier, (ii) excellent bioactivity with respect to cell-protecting activity, (iii) a low manufacturing cost, thus being economically advantageous, and (iv) no side effects on cell proliferation. Also, a pharmaceutical composition comprising the erythropoietin-derived peptide described herein as an active ingredient is described. The pharmaceutical composition may be used for preventing or treating cell damage-related illnesses, such as stroke, mechanical damage or ischemic damage to the nervous system, myocardial infarction, retinal damage, and diabetes. Also, the described pharmaceutical composition may be used for preventing cell damage.

7 Claims, 14 Drawing Sheets
Specification includes a Sequence Listing.

(51) Int. Cl.
  G01N 33/53 (2006.01)
  G01N 33/567 (2006.01)
  C07K 14/505 (2006.01)
  C12N 15/86 (2006.01)
  C07K 14/47 (2006.01)
  A61P 25/28 (2006.01)
  A61P 25/02 (2006.01)
  A61P 21/00 (2006.01)
  A61P 25/00 (2006.01)
  A61P 9/00 (2006.01)
  G01N 33/50 (2006.01)
  C07K 14/71 (2006.01)
  A61K 38/17 (2006.01)
  G01N 33/68 (2006.01)
  A61K 47/64 (2017.01)
  A61K 39/00 (2006.01)
  A61K 9/10 (2006.01)
  C12P 21/02 (2006.01)
  C07K 14/435 (2006.01)
  C12N 15/85 (2006.01)
  C07K 7/08 (2006.01)

(56) References Cited

U.S. PATENT DOCUMENTS

| 2008/0260746 | A1* | 10/2008 | Abderrahim | C07K 14/505 424/139.1 |
| 2009/0197801 | A1* | 8/2009 | Berezin | C07K 14/505 514/8.3 |
| 2009/0221482 | A1 | 9/2009 | Cerami et al. | |
| 2013/0123174 | A1* | 5/2013 | Berezin | C07K 14/505 514/8.3 |
| 2014/0378378 | A1* | 12/2014 | Kim | C07K 14/505 514/7.7 |
| 2015/0238556 | A1* | 8/2015 | Berezin | C07K 14/505 514/17.8 |
| 2019/0135913 | A1 | 5/2019 | Ghosh et al. | |
| 2019/0375810 | A1* | 12/2019 | Moon | C12N 15/86 |

FOREIGN PATENT DOCUMENTS

| KR | 10-2015-0090101 | | 8/2015 |
| WO | WO 2006/119767 A2 | | 11/2006 |
| WO | WO2006119767 | * | 11/2006 |
| WO | WO2006120030 | * | 11/2006 |
| WO | WO 2018/155997 A1 | | 8/2018 |

OTHER PUBLICATIONS

Schmidt et al. Annu. Rev. Biomed. Eng. 2003. 5: 293-347.*
Hoke et al. Nat. Clin. Pract. Neurol. 2006: 448-454.*
Syed et al., Nature, 1998; 395:511-516.*
Sytkowski, A.J., et al., "Immunochemical Studies of Human Erythropoietin Using Site-specific Anti-peptide Antibodies," *The Journal of Biological Chemistry*, 262(3):1161-1165 (1987).
International Search Report (and English translation) received in PCT Application No. PCT/KR2018/002396 dated Jun. 4, 2018.
(*)Written Opinion received in PCT Application No. PCT/KR2018/002396 dated Jun. 4, 2018 in Korean language.
GenBank: ANC33499.2, "10F7-linker-EPO(K45D), partial [synthetic construct]," XP055537041, retrieved from NCBI Database accession No. ANC33499.2 (Jun. 24, 2016).
Yoo, S-J, et al., "Neuroprotective Effects of an Erythropoietin-Derived Peptide in PC12 Cells under Oxidative Stress," *CNS & Neurological Disorders, Drug Targets*, 15:927-934 (2016).
Pankratova, S., et al., "Neuroprotective properties of a novel, non-haematopoietic agonist of the erythropoietin receptor," *Brain*, 133:2281-2294 (2010).
Dmytriyeva, O., et al., "Epobis is a Nonerythropoietic and Neuroprotective Agonist of the Erythropoietin Receptor with Anti-Inflammatory and Memory Enhancing Effects," *Mediators of Inflammation*, Article ID 1346390, 11 pages (2016).

* cited by examiner

SEQUENCE LISTING

<160> NUMBER OF SEQ ID NOS: 25

<210> SEQ ID NO 1
<211> LENGTH: 23
<212> TYPE: PRT
<213> ORGANISM: Artificial Sequence

```
<220> FEATURE:
<223> OTHER INFORMATION: peptide ML1

<400> SEQUENCE: 1

Leu Gln Leu His Val Asp Lys Ala Val Ser Gly Leu Arg Ser Leu Thr
1               5                   10                  15

Thr Leu Leu Arg Ala Leu Gly
            20

<210> SEQ ID NO 2
<211> LENGTH: 20
<212> TYPE: PRT
<213> ORGANISM: Artificial Sequence
<220> FEATURE:
<223> OTHER INFORMATION: peptide ML2

<400> SEQUENCE: 2

Leu His Val Asp Lys Ala Val Ser Gly Leu Arg Ser Leu Thr Thr Leu
1               5                   10                  15

Leu Arg Ala Leu
            20

<210> SEQ ID NO 3
<211> LENGTH: 10
<212> TYPE: PRT
<213> ORGANISM: Artificial Sequence
<220> FEATURE:
<223> OTHER INFORMATION: peptide ML3

<400> SEQUENCE: 3

Thr Lys Val Asn Phe Tyr Ala Trp Lys Arg
1               5                   10

<210> SEQ ID NO 4
<211> LENGTH: 24
<212> TYPE: PRT
<213> ORGANISM: Artificial Sequence
<220> FEATURE:
<223> OTHER INFORMATION: peptide ML4

<400> SEQUENCE: 4

Asp Lys Ala Val Ser Gly Leu Arg Ser Leu Thr Thr Leu Leu Arg Ala
1               5                   10                  15

Leu Gly Ala Gln Lys Glu Ala Ile
            20

<210> SEQ ID NO 5
<211> LENGTH: 14
<212> TYPE: PRT
<213> ORGANISM: Artificial Sequence
<220> FEATURE:
<223> OTHER INFORMATION: peptide ML5

<400> SEQUENCE: 5

Ser Gly Leu Arg Ser Leu Thr Thr Leu Leu Arg Ala Leu Gly
1               5                   10

<210> SEQ ID NO 6
<211> LENGTH: 20
<212> TYPE: PRT
<213> ORGANISM: Artificial Sequence
<220> FEATURE:
<223> OTHER INFORMATION: peptide ML6

<400> SEQUENCE: 6
```

```
Ser Gly Leu Arg Ser Leu Thr Thr Leu Leu Arg Ala Leu Gly Ala Gln
1               5                   10                  15

Lys Glu Ala Ile
            20
```

<210> SEQ ID NO 7
<211> LENGTH: 25
<212> TYPE: PRT
<213> ORGANISM: Artificial Sequence
<220> FEATURE:
<223> OTHER INFORMATION: peptide ML7

<400> SEQUENCE: 7

```
Trp Glu Pro Leu Gln Leu His Val Asp Lys Ala Val Ser Gly Leu Arg
1               5                   10                  15

Ser Leu Thr Thr Leu Leu Arg Ala Leu
            20                  25
```

<210> SEQ ID NO 8
<211> LENGTH: 17
<212> TYPE: PRT
<213> ORGANISM: Artificial Sequence
<220> FEATURE:
<223> OTHER INFORMATION: peptide ML8

<400> SEQUENCE: 8

```
Asp Lys Ala Val Ser Gly Leu Arg Ser Leu Thr Thr Leu Leu Arg Ala
1               5                   10                  15

Leu
```

<210> SEQ ID NO 9
<211> LENGTH: 23
<212> TYPE: PRT
<213> ORGANISM: Artificial Sequence
<220> FEATURE:
<223> OTHER INFORMATION: peptide ML1-1

<400> SEQUENCE: 9

```
Leu Gln Leu His Val Leu Lys Arg Val Ser Gly Leu Leu Ser His Thr
1               5                   10                  15

Met Leu Leu Lys Ala Leu Gly
            20
```

<210> SEQ ID NO 10
<211> LENGTH: 20
<212> TYPE: PRT
<213> ORGANISM: Artificial Sequence
<220> FEATURE:
<223> OTHER INFORMATION: peptide ML2-1

<400> SEQUENCE: 10

```
Arg His Val Gln Lys Ala Glu Ser Gly Leu Arg Ser Leu Thr Lys Leu
1               5                   10                  15

Leu Arg Glu Leu
            20
```

<210> SEQ ID NO 11
<211> LENGTH: 10
<212> TYPE: PRT
<213> ORGANISM: Artificial Sequence
<220> FEATURE:
<223> OTHER INFORMATION: peptide ML3-1

<400> SEQUENCE: 11

Thr Arg Val Asn Tyr Gln Ala Trp Lys Arg
1               5                  10

<210> SEQ ID NO 12
<211> LENGTH: 24
<212> TYPE: PRT
<213> ORGANISM: Artificial Sequence
<220> FEATURE:
<223> OTHER INFORMATION: peptide ML4-1

<400> SEQUENCE: 12

Lys Lys Ala Val Ser Gly Leu Lys Thr Leu Thr His Ile Leu Arg Ala
1               5                  10                  15

Leu Gly Ala Gln Lys Glu Ala Ile
            20

<210> SEQ ID NO 13
<211> LENGTH: 14
<212> TYPE: PRT
<213> ORGANISM: Artificial Sequence
<220> FEATURE:
<223> OTHER INFORMATION: peptide ML5-1

<400> SEQUENCE: 13

Ala Gly Leu Arg Ser Arg Ala His Leu Arg Arg Ala Leu Ala
1               5                  10

<210> SEQ ID NO 14
<211> LENGTH: 20
<212> TYPE: PRT
<213> ORGANISM: Artificial Sequence
<220> FEATURE:
<223> OTHER INFORMATION: peptide ML6-1

<400> SEQUENCE: 14

Lys Gly Leu Arg Ser Leu Ile Ser Leu Leu Arg Ala Leu Gly Ala Gln
1               5                  10                  15

Lys Glu Ala Ile
            20

<210> SEQ ID NO 15
<211> LENGTH: 25
<212> TYPE: PRT
<213> ORGANISM: Artificial Sequence
<220> FEATURE:
<223> OTHER INFORMATION: peptide ML7-1

<400> SEQUENCE: 15

Asp Glu Ala Leu Asp Leu Glu Val Asp Lys Ala Ala Thr Gly Leu Arg
1               5                  10                  15

Thr Leu Thr Thr Leu Ile Arg Ala Leu
            20                  25

<210> SEQ ID NO 16
<211> LENGTH: 13
<212> TYPE: PRT
<213> ORGANISM: Artificial Sequence
<220> FEATURE:
<223> OTHER INFORMATION: peptide ML8-1

<400> SEQUENCE: 16

Asn Lys Ala Val Ala Gly Leu Arg Ser Leu Thr Val Asn
1               5                  10

<210> SEQ ID NO 17

```
<211> LENGTH: 23
<212> TYPE: PRT
<213> ORGANISM: Artificial Sequence
<220> FEATURE:
<223> OTHER INFORMATION: peptide ML1-H1

<400> SEQUENCE: 17

Leu Gln Leu His Val Leu Lys Ala Val Ser Gly Leu Leu Thr His Thr
1               5                   10                  15

Thr Leu Leu Lys Ala Leu Gly
            20

<210> SEQ ID NO 18
<211> LENGTH: 23
<212> TYPE: PRT
<213> ORGANISM: Artificial Sequence
<220> FEATURE:
<223> OTHER INFORMATION: peptide ML1-H2

<400> SEQUENCE: 18

Leu Gln Leu His Val Leu Lys Ala Val Ser Gly Leu Leu Thr Leu Thr
1               5                   10                  15

Met Ile Arg Arg Ala Leu Gly
            20

<210> SEQ ID NO 19
<211> LENGTH: 23
<212> TYPE: PRT
<213> ORGANISM: Artificial Sequence
<220> FEATURE:
<223> OTHER INFORMATION: peptide ML1-H3

<400> SEQUENCE: 19

Leu Gln Leu His Val Leu Lys Ala Val Ala Gly Leu Arg Thr Leu Ala
1               5                   10                  15

Met Ile Arg Arg Ala Leu Ala
            20

<210> SEQ ID NO 20
<211> LENGTH: 23
<212> TYPE: PRT
<213> ORGANISM: Artificial Sequence
<220> FEATURE:
<223> OTHER INFORMATION: peptide ML1-C1

<400> SEQUENCE: 20

Leu Asp Leu Glu Val Asp Lys Ala Val Ser Gly Leu Arg Ser Leu Thr
1               5                   10                  15

Thr Leu Leu Arg Ala Leu Gly
            20

<210> SEQ ID NO 21
<211> LENGTH: 23
<212> TYPE: PRT
<213> ORGANISM: Artificial Sequence
<220> FEATURE:
<223> OTHER INFORMATION: peptide ML1-C2

<400> SEQUENCE: 21

Leu Gln Arg His Val Asp Lys Arg Val Ser Gly Leu Arg Ser Leu Thr
1               5                   10                  15

Thr Leu Leu Arg Ala Leu Gly
            20
```

```
<210> SEQ ID NO 22
<211> LENGTH: 23
<212> TYPE: PRT
<213> ORGANISM: Artificial Sequence
<220> FEATURE:
<223> OTHER INFORMATION: peptide ML1-C3

<400> SEQUENCE: 22

Leu Gln Arg His Val Lys Lys Arg Val Lys Gly Leu Lys Ser Leu Thr
1               5                   10                  15

Thr Leu Leu Arg Ala Leu Gly
            20

<210> SEQ ID NO 23
<211> LENGTH: 16
<212> TYPE: PRT
<213> ORGANISM: Artificial Sequence
<220> FEATURE:
<223> OTHER INFORMATION: peptide ML1-L2

<400> SEQUENCE: 23

Leu His Val Asp Lys Ala Val Ser Gly Leu Arg Ser Leu Thr Thr Leu
1               5                   10                  15

<210> SEQ ID NO 24
<211> LENGTH: 16
<212> TYPE: PRT
<213> ORGANISM: Artificial Sequence
<220> FEATURE:
<223> OTHER INFORMATION: peptide ML1-K2

<400> SEQUENCE: 24

Lys His Val Asp Lys Ala Val Ser Gly Leu Arg Ser Leu Thr Thr Lys
1               5                   10                  15

<210> SEQ ID NO 25
<211> LENGTH: 16
<212> TYPE: PRT
<213> ORGANISM: Artificial Sequence
<220> FEATURE:
<223> OTHER INFORMATION: peptide ML1-R2

<400> SEQUENCE: 25

Arg His Val Asp Lys Ala Val Ser Gly Leu Arg Ser Leu Thr Thr Arg
1               5                   10                  15
```

ERYTHROPOIETIN-DERIVED PEPTIDES AND METHODS OF PROTECTING CELLS FROM OXIDATIVE DAMAGE INDUCED BY REACTIVE OXYGEN SPECIES

RELATED APPLICATIONS

The present application is a continuation application of International Application No. PCT/KR2018/002396, filed Feb. 27, 2018, which claims priority from Korean Patent Application No. 10-2017-0025370, filed on Feb. 27, 2017, the disclosure of which are hereby incorporated by reference herein in their entirety.

SEQUENCE LISTING

This application is being filed electronically via EFS-Web and includes an electronically submitted Sequence Listing in .txt format. The .txt file contains a sequence listing entitled "16458_7_Seq_Listing_ST25" created on Aug. 23, 2019 and is 8000 bytes in size. The sequence listing contained in this .txt file is part of the specification and hereby incorporated by reference in its entirety.

BACKGROUND

The present disclosure relates to an erythropoietin (EPO)-derived peptide of which a side effect of cell proliferation is eliminated, and a pharmaceutical composition for preventing or treating a neurodegenerative disease, the pharmaceutical composition including the EPO-derived peptide.

During lifetime, the human body is consistently exposed to stimuli, which are harmful to the human body. In response to such exposure, the individual protects their body. Harmful stimuli include various stimuli such as hypoxia, infection, mechanical stimulations, etc. Defense mechanisms against such stimuli exist at a cellular level. Various cytokines that are secreted as a defense mechanism against stimuli play a role in protecting an individual by killing abnormal cells produced due to exposure to stimuli or by preventing death of normal cells.

Erythropoietin (EPO) is a glycoprotein having a molecular weight of about 30,000, and is a hematopoietic cytokine which promotes differentiation of red blood cell precursors and increases the number of red blood cells to exhibit an effect of preventing or improving anemia. This protein initiates its function by binding to a receptor of red blood cell precursors and induces an increase in intracellular calcium ions, an increase in DNA biosynthesis, stimulation of hemoglobin production, etc. Therefore, EPO may be used as a therapeutic agent for anemia such as anemia in patients with a renal disease, anemia in premature babies, anemia associated with hypothyroidism, anemia associated with malnutrition, anemia associated with chronic renal failure, postoperative anemia, etc.

Beyond anemia management, EPO has been recently considered as a therapeutic agent for neurological damage. EPO has exhibited tissue protective ability with respect to nervous system damage, and has also exhibited an effect of reducing tissue damage in an animal model of acute myocardial infarction.

However, in addition to the therapeutic effect on anemia and the ability to protect nerve cells and nervous tissue, it has been found that an increase in red blood cells and an increase in platelet activity may occur when EPO is injected into the human body. These adverse effects may lead to a decrease in the tissue protective ability of EPO. Accordingly, research is being conducted into the development of modified EPO or peptides including a partial structure of EPO such as asialo-EPO, carbamylated EPO, EPOtris, EPObis, etc., which are capable of maintaining the tissue protective ability without increasing red blood cells or stimulating platelet activity.

As described above, EPO is known to have a therapeutic effect on anemia, an ability to protect nerve cells or nervous tissue, and an ability to protect myocardial tissue. EPO is a very active protein, but has a very high production cost. When EPO is injected into peripheral blood vessels, EPO may not be transported to a target organ due to a tissue-blood barrier present in certain target organs, which causes difficulties in drug delivery. Accordingly, there is a need for an effective human EPO substitute having low production costs and capable of being easily transported to biological tissues.

Accordingly, the present inventors have prepared a human erythropoietin-derived peptide having lower production costs than natural erythropoietin and the ability to easily pass through the tissue-blood barrier in the body while maintaining the cell or tissue protective abilities of natural human erythropoietin without inducing the side effect of cell proliferation.

SUMMARY

An aspect provides a peptide, which is described by any one amino acid sequence selected from the group consisting of SEQ ID NOS: 1 to 25.

Another aspect provides a pharmaceutical composition for preventing or treating a neurodegenerative disease, the pharmaceutical composition including, as an active ingredient, the peptide, one or more polynucleotides encoding the peptide, a vector including the polynucleotide, or a host cell including the vector.

Still another aspect provides a method of preventing or treating a neurodegenerative disease, the method including administering the composition including, as an active ingredient, the peptide, one or more polynucleotides encoding the peptide, the vector including the polynucleotide, or the host cell including the vector.

Still another aspect provides use of the composition including, as an active ingredient, the peptide, one or more polynucleotides encoding the peptide, the vector including the polynucleotide, or the host cell including the vector in the preparation of a prophylactic or therapeutic agent for a neurodegenerative disease.

BRIEF DESCRIPTION OF DRAWINGS

FIG. 1A: determination of binding affinities of ML6-1, ML4-1, ML2-1, and ML3-1,

FIG. 1B: determination of binding affinities of ML1-1, ML8-1, ML7-1, and ML5-1,

FIG. 1C: determination of binding affinities of ML1, ML1-H1, ML1-H2, and ML1-H3, and FIG. 1D: determination of binding affinities of ML1, ML1-C1, ML1-C2, and ML1-C3;

FIG. 2A: effects of treatment with ML1-1, ML4-1, ML6-1, and ML8-1,

FIG. 2B: effects of treatment with ML2-1, ML3-1, ML5-1, and ML7-1,

Figure 1A:
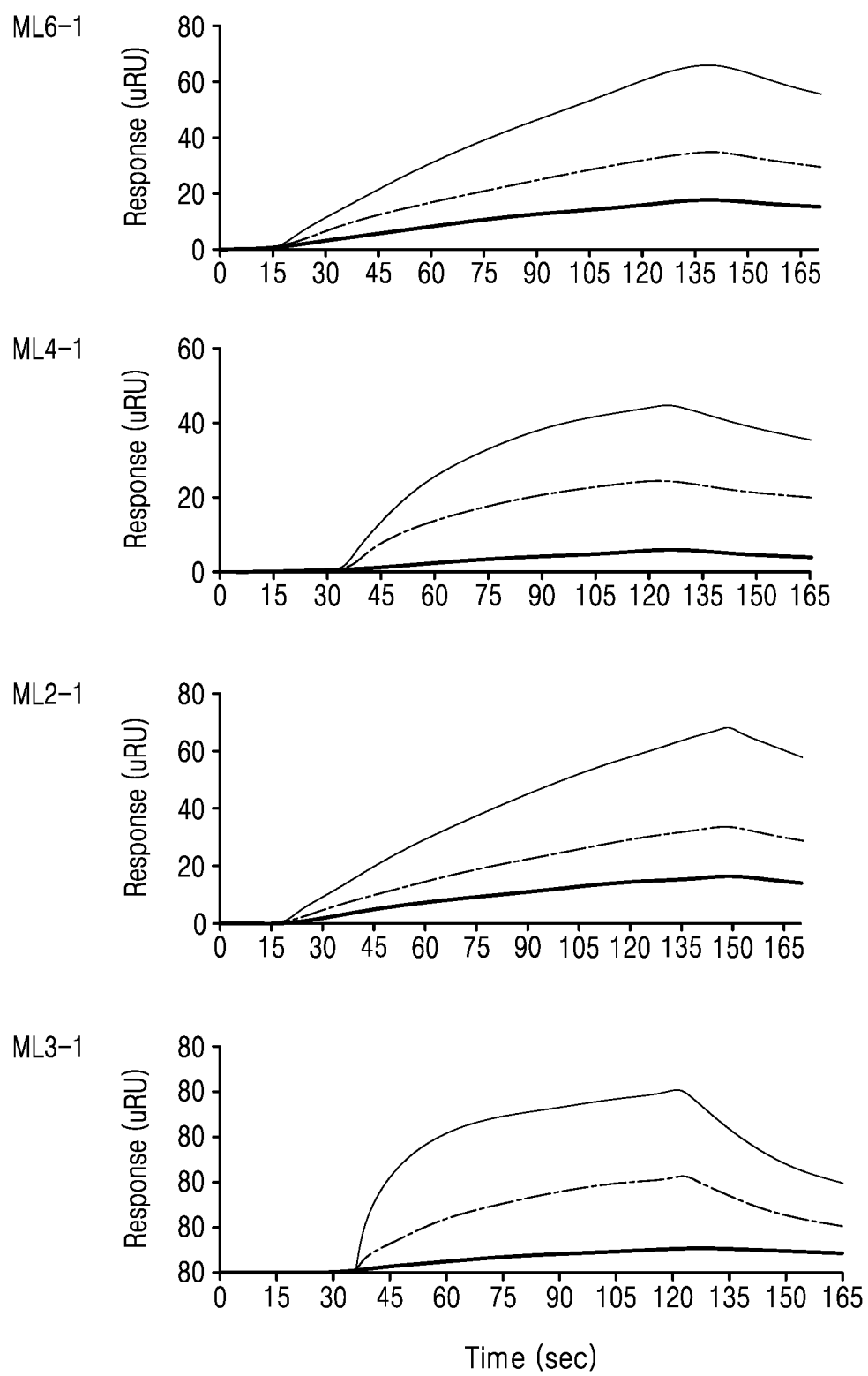
FIGS. 1A-1D depict graphs showing binding affinities measured by a surface plasmon resonance (SPR) technique to determine whether erythropoietin-derived peptides act on the erythropoietin receptor.
Figure 1B:
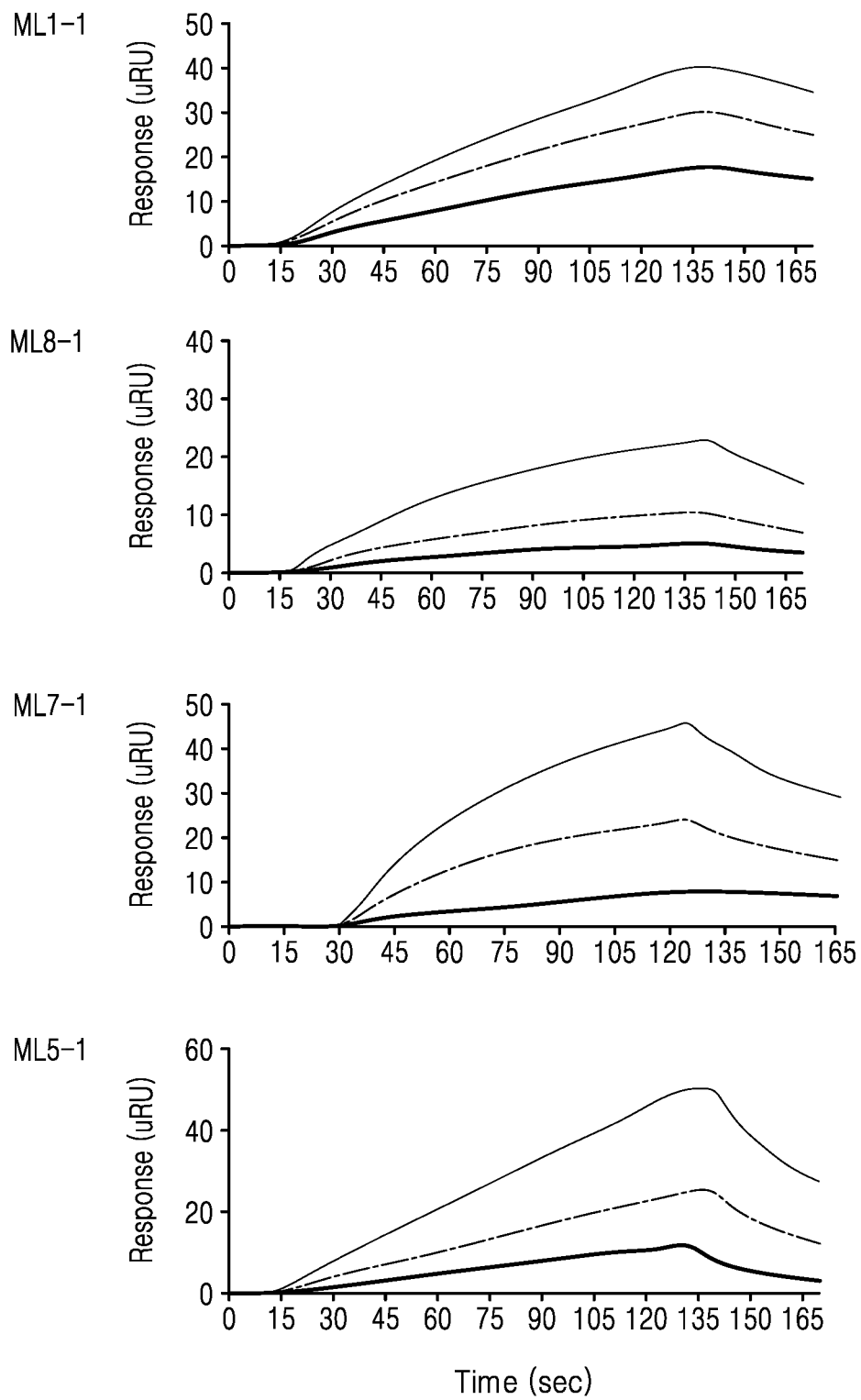
Figure 1C:
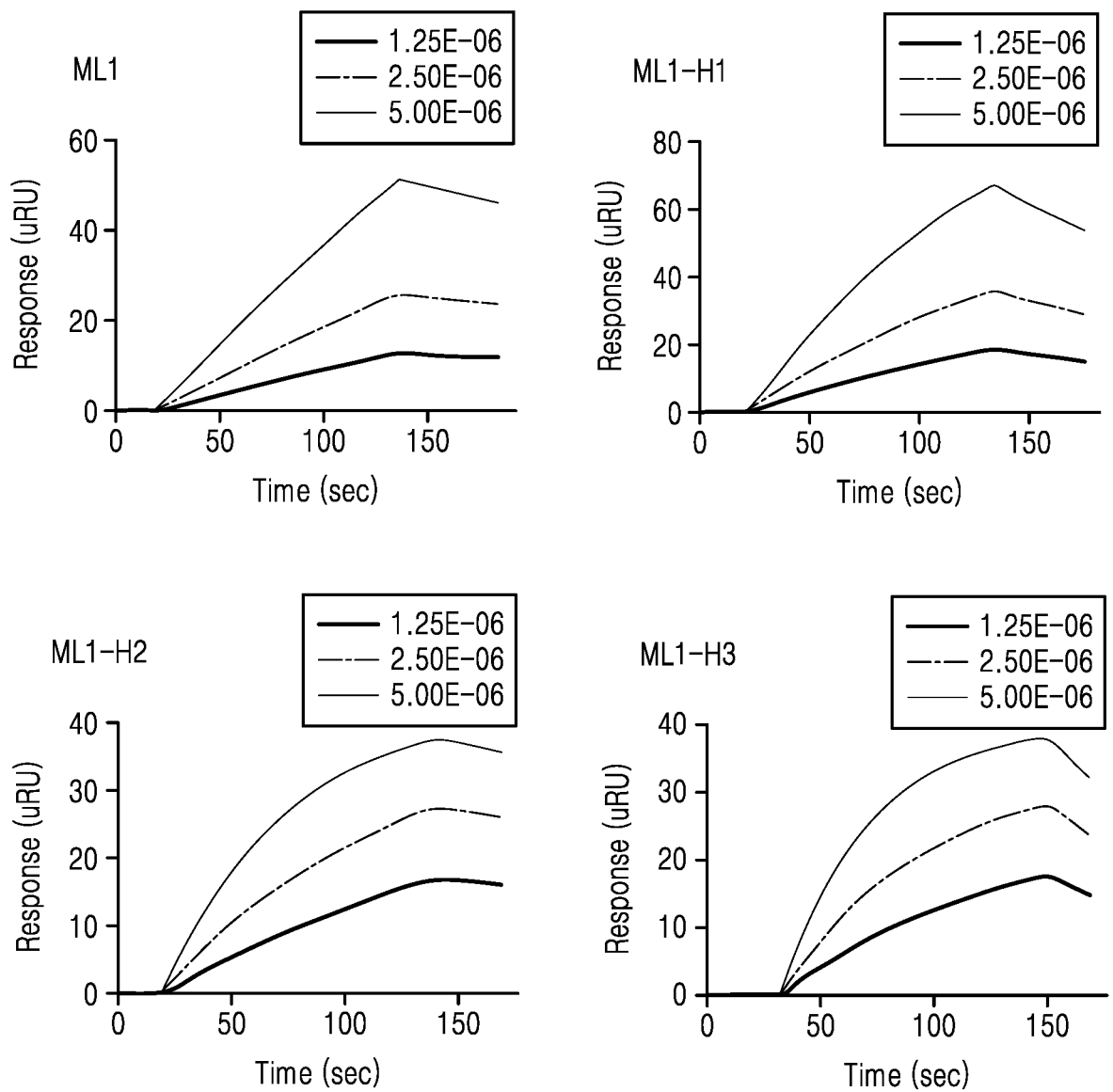
Figure 1D:
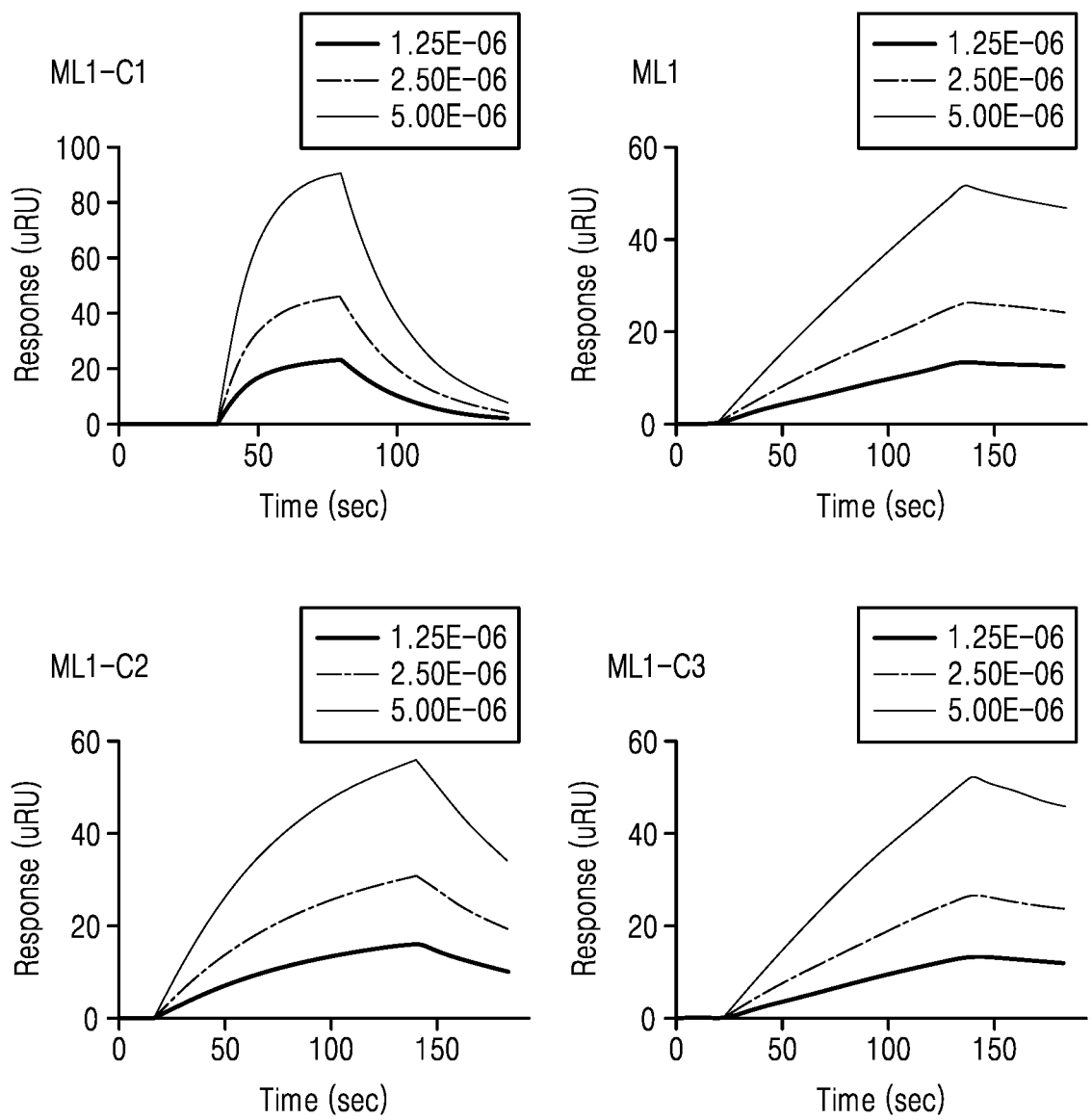
Figure 2A:
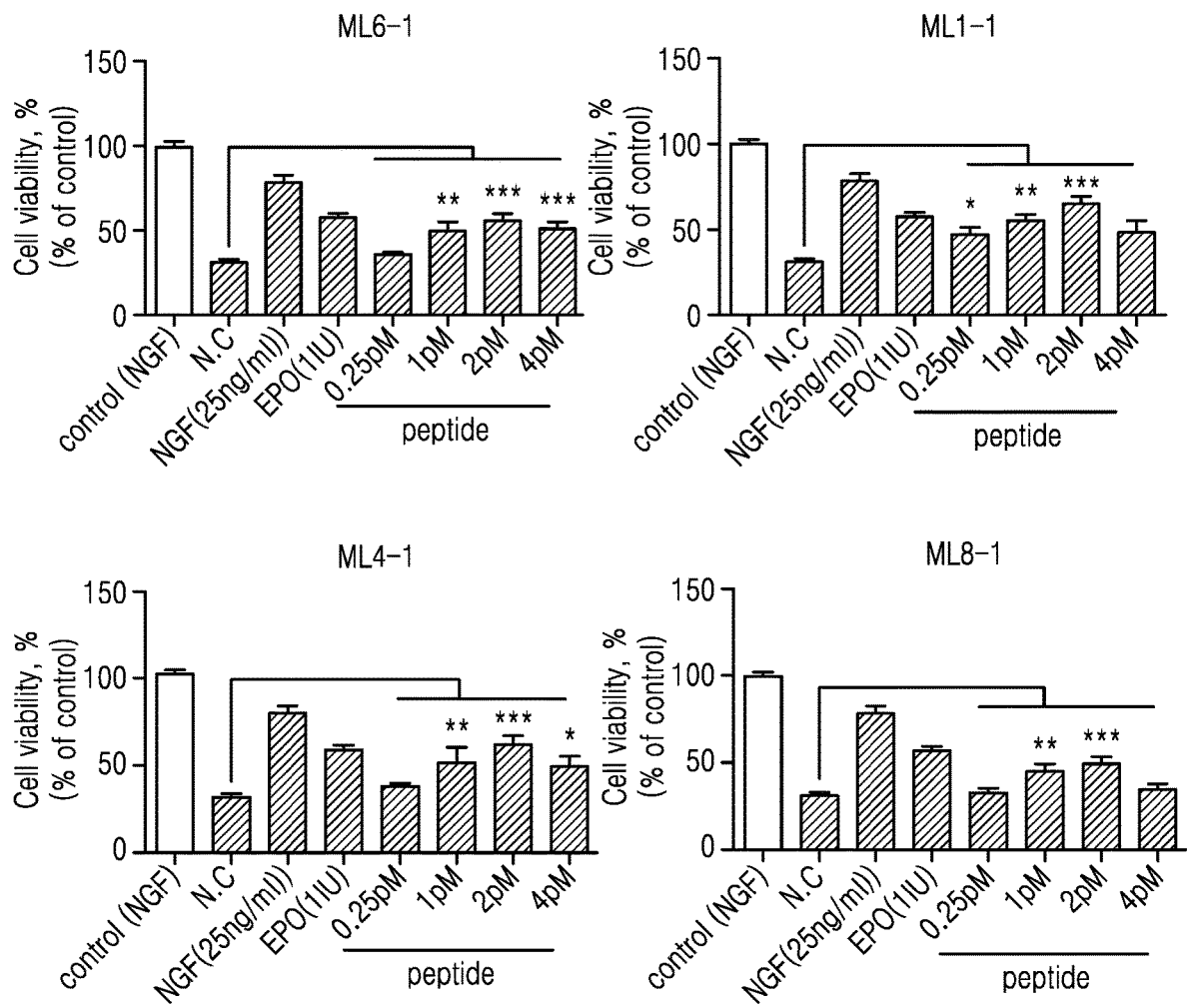
FIGS. 2A-2D depict graphs showing cell protective effects of erythropoietin-derived peptide treatment of cells in which reactive oxygen species were increased by hydrogen peroxide.
Figure 2B:
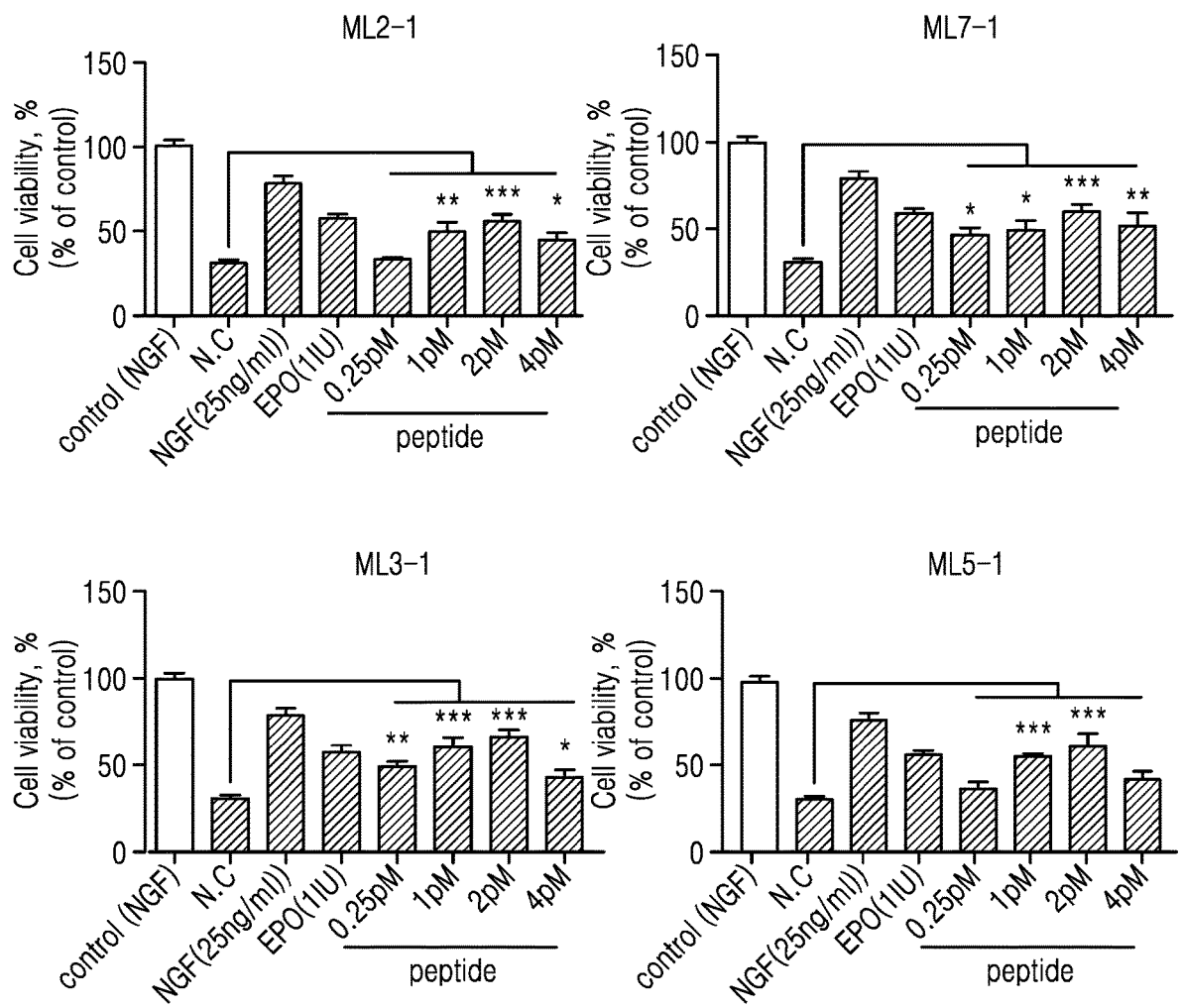
Figure 2C:
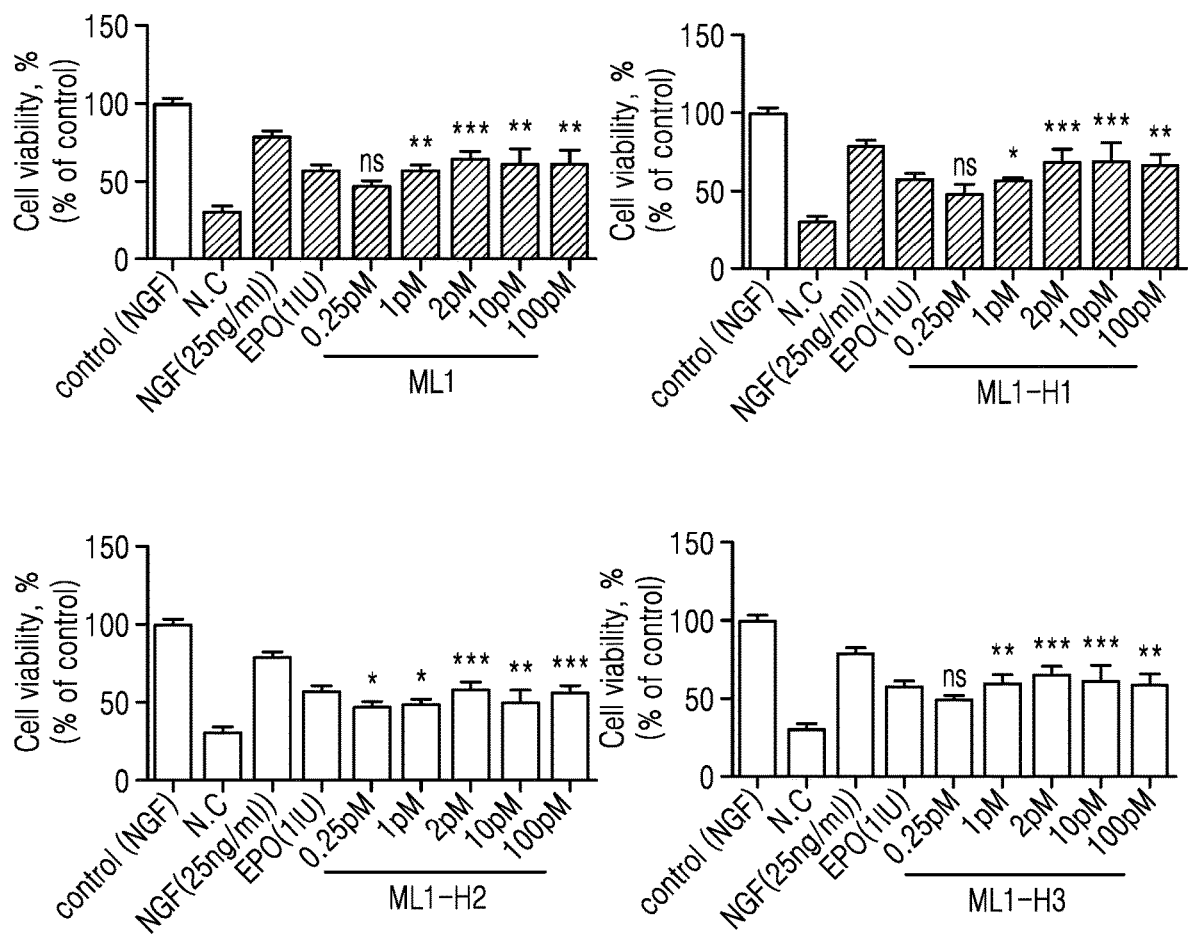
Figure 2D:
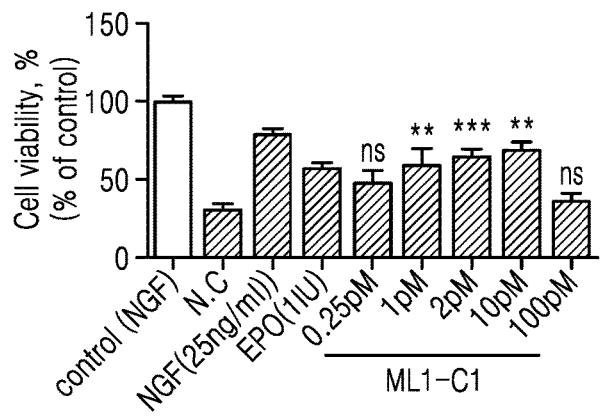
Figure 2D:
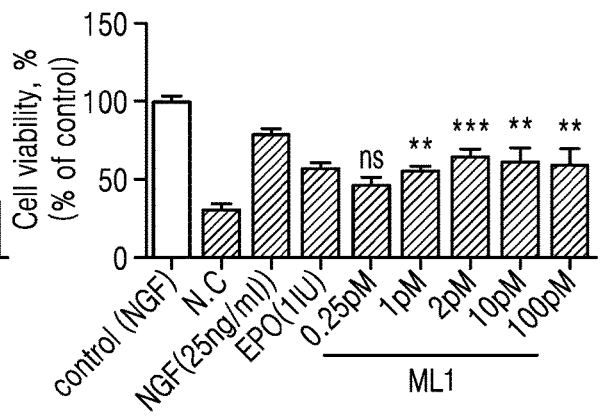
Figure 2D:
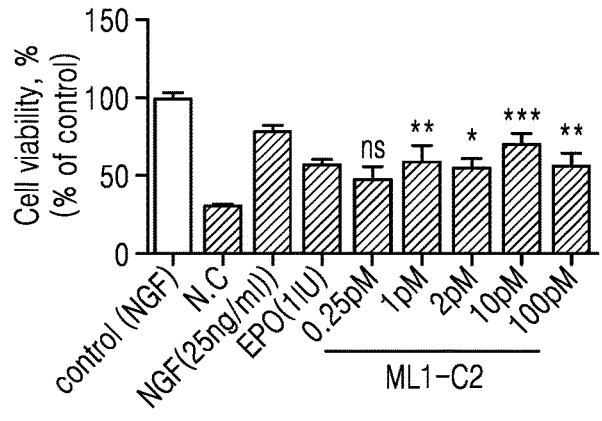
Figure 2D:
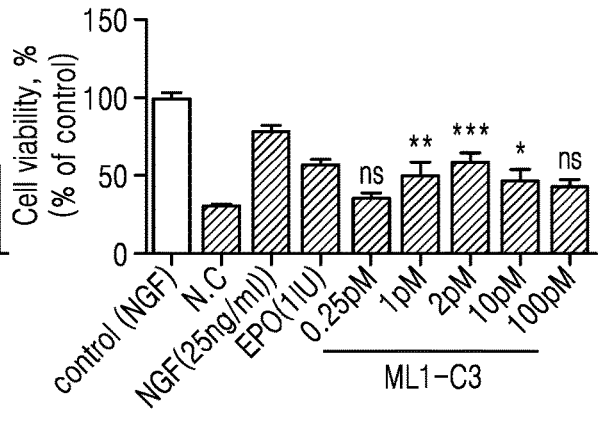
Figure 3A:
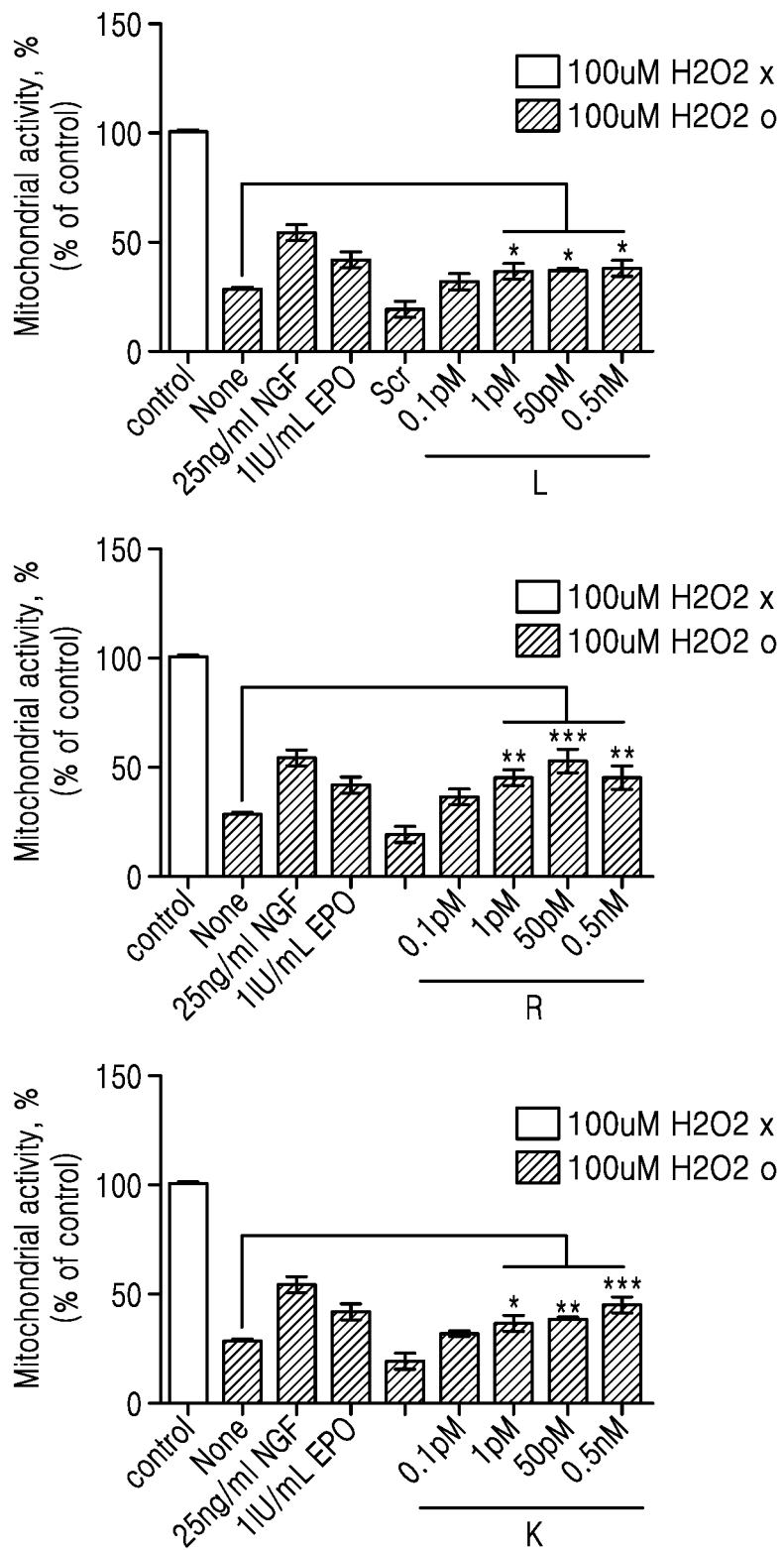
Figure 3B:
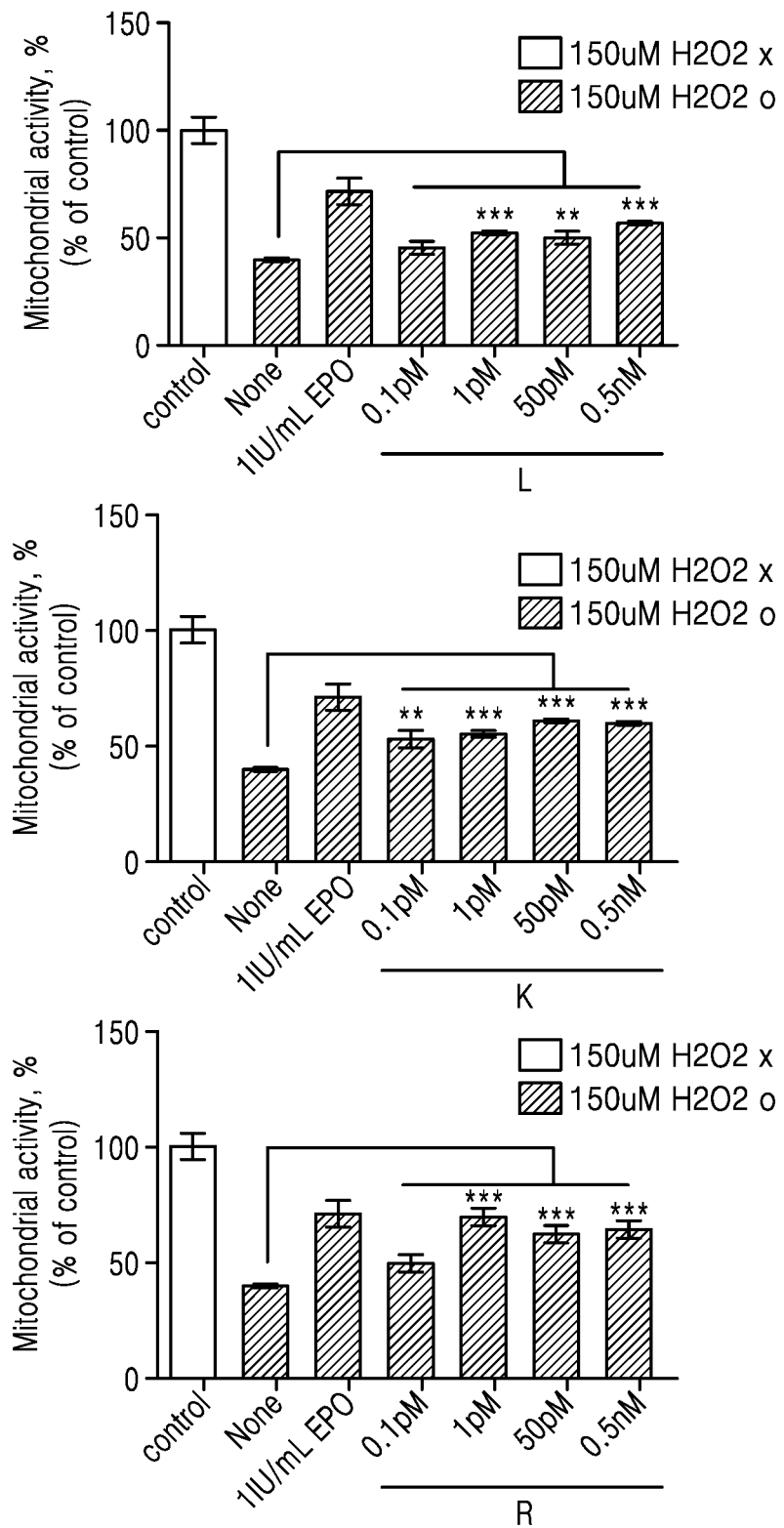
Figure 4:
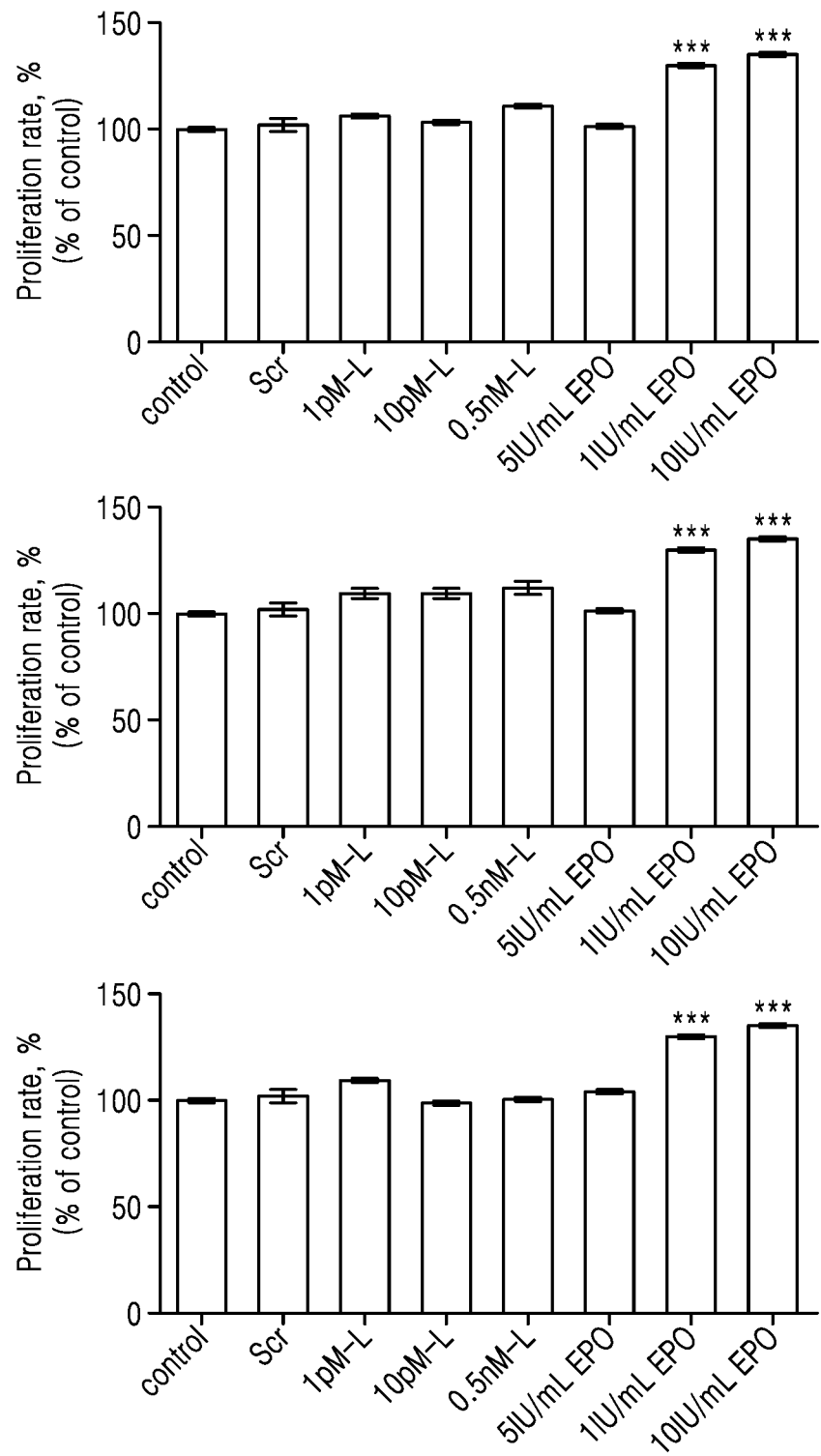
Figure 5:
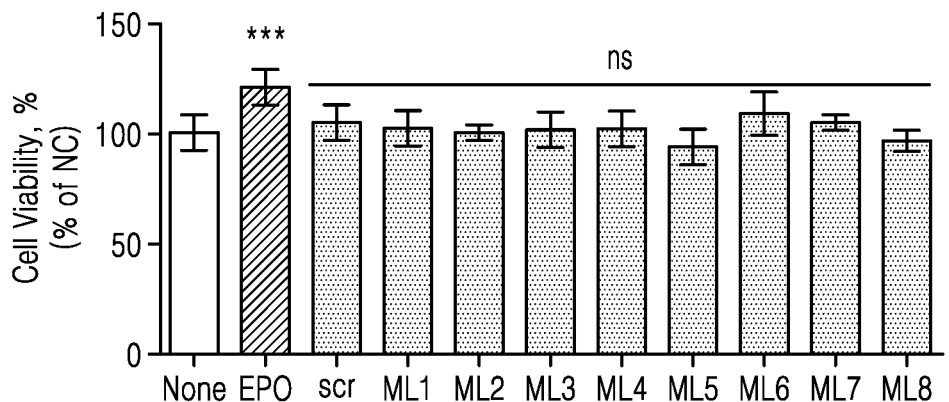
Figure 5:
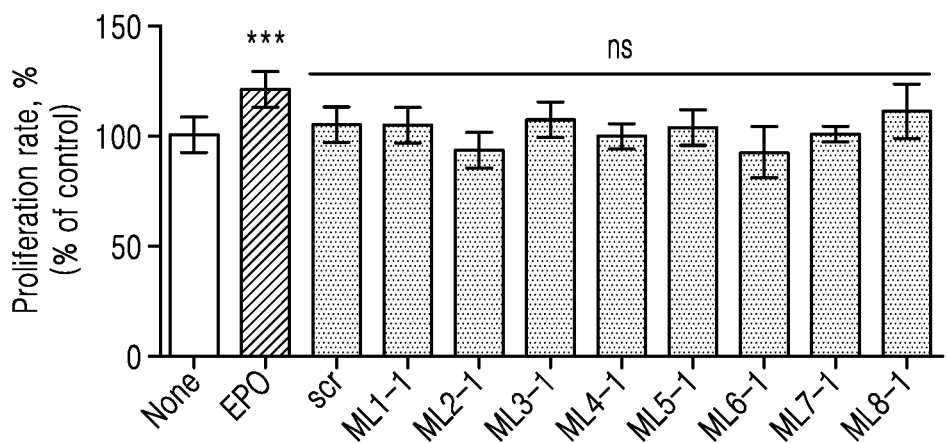
Figure 5:
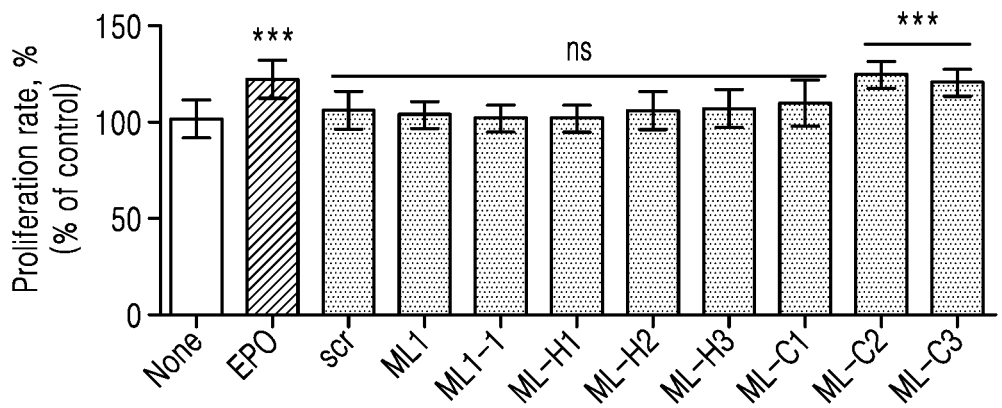
Figure 6:
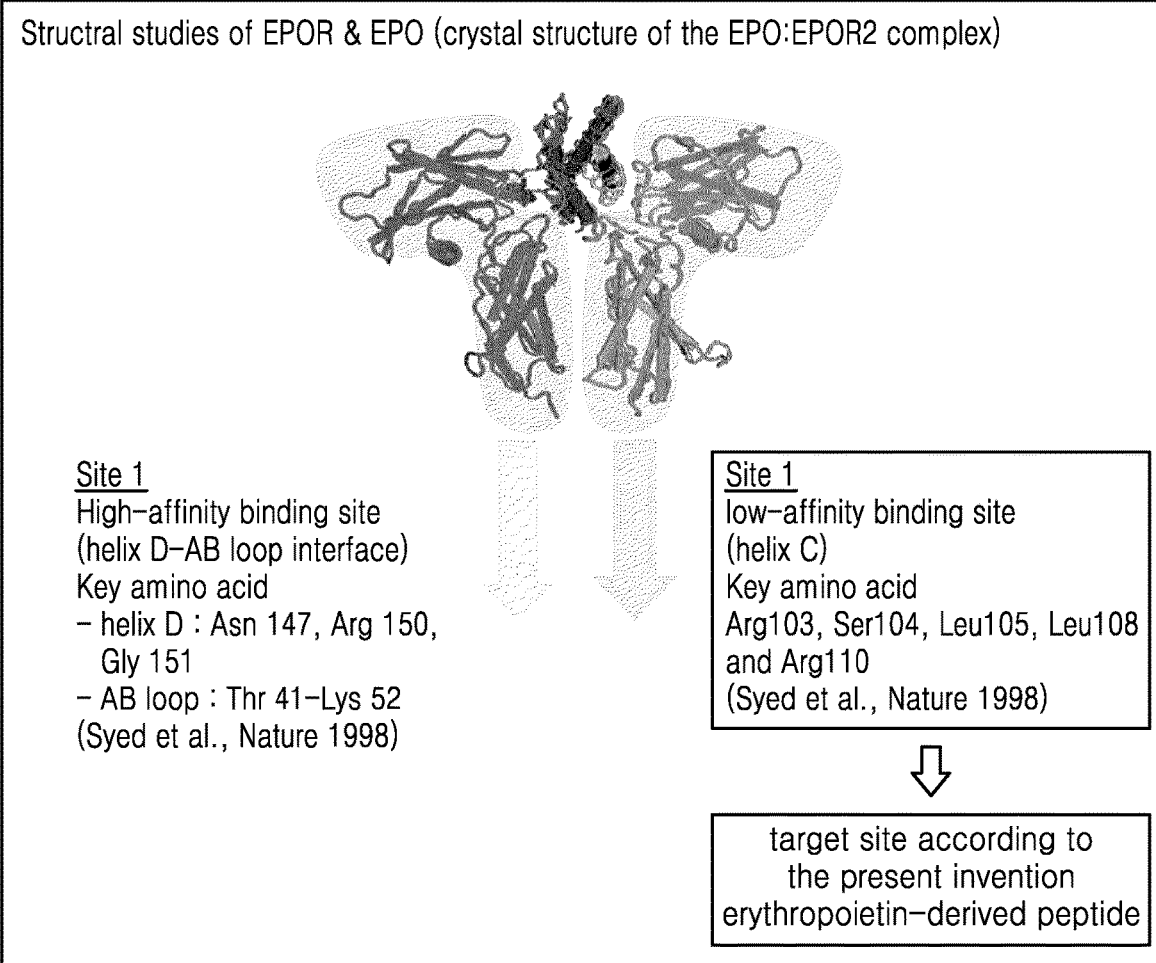
Figure 7:
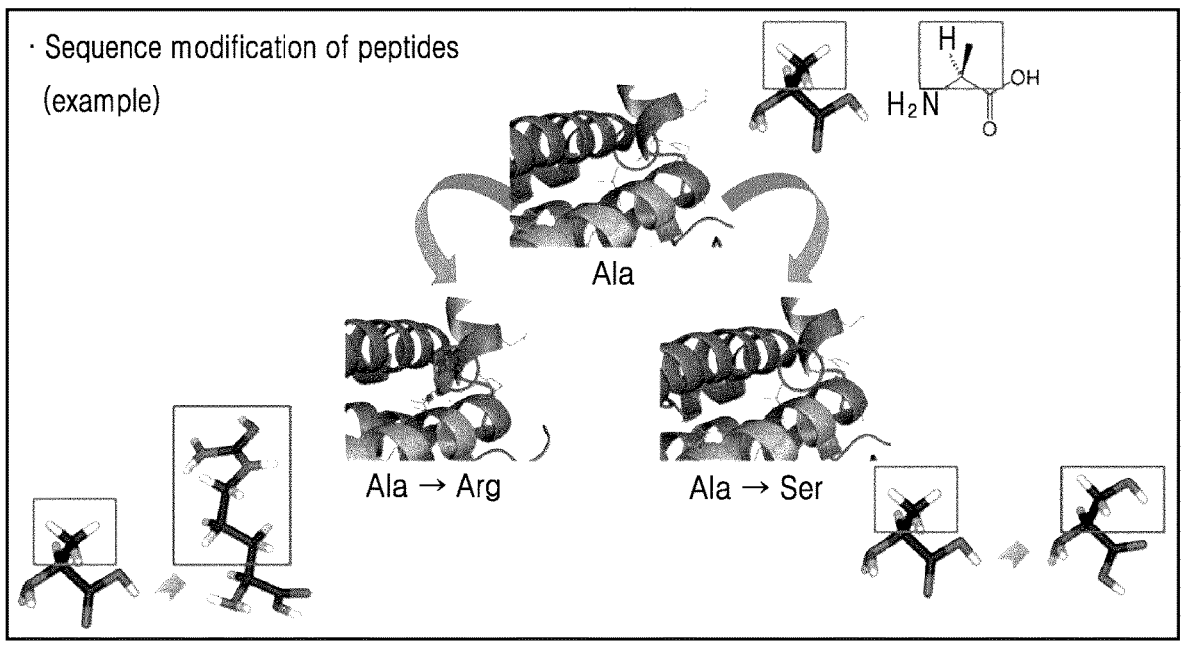

Control (NGF): cells treated with nerve growth factor (NGF) as a control group,

N.C: cells treated with hydrogen peroxide,

NGF (25 ng/ml): cells treated with NGF after treatment with hydrogen peroxide,

EPO (1 IU): an experimental group treated with 1 IU/ml of natural erythropoietin after treatment with hydrogen peroxide, 0.25 pM: an experimental group treated with 0.25 pM of the peptide of the present disclosure after treatment with hydrogen peroxide, 1 pM: an experimental group treated with 1 pM of the peptide of the present disclosure after treatment with hydrogen peroxide, 2 pM: an experimental group treated with 2 pM of the peptide of the present disclosure after treatment with hydrogen peroxide, 4 pM: an experimental group treated with 4 pM of the peptide of the present disclosure after treatment with hydrogen peroxide, FIG. 2C: effects of treatment with ML1, ML1-H1, ML1-H2, and ML1-H3, FIG. 2D: effects of treatment with ML1, ML1-C1, ML1-C2, and ML1-C3, Control (NGF): cells treated with NGF as a control group, N.C: cells treated with hydrogen peroxide, NGF (25 ng/ml): cells treated with NGF after treatment with hydrogen peroxide, EPO (1 IU): an experimental group treated with 1 IU/ml of natural erythropoietin after treatment with hydrogen peroxide, 0.25 pM: an experimental group treated with 0.25 pM of the peptide of the present disclosure after treatment with hydrogen peroxide, 1 pM: an experimental group treated with 1 pM of the peptide of the present disclosure after treatment with hydrogen peroxide, 2 pM: an experimental group treated with 2 pM of the peptide of the present disclosure after treatment with hydrogen peroxide, 10 pM: an experimental group treated with 10 pM of the peptide of the present disclosure after treatment with hydrogen peroxide, and 100 pM: an experimental group treated with 100 pM of the peptide of the present disclosure after treatment with hydrogen peroxide;

FIGS. 3A and 3B depict graphs showing cell protective effects of peptides (ML1-L2, ML1-K2, and ML1-R2) prepared by partially modifying sequences of an erythropoietin-derived ML1 peptide:

FIG. 3A: cell protective effects in differentiated PC12 cells,

FIG. 3B: cell protective effects in human SH-SY5Y cells,

Control: non-treated cells as a control group,

None: cells treated with hydrogen peroxide,

NGF (25 ng/mL): cells treated with NGF after treatment with hydrogen peroxide, as a positive control group, EPO (1 IU/mL): an experimental group treated with 1 IU/ml of natural erythropoietin after treatment with hydrogen peroxide, Scr: cells treated with 1 pM of scrambled (Scr) peptide after treatment with hydrogen peroxide, as a negative control group, 0.1 pM: an experimental group treated with 0.1 pM of the peptide of the present disclosure after treatment with hydrogen peroxide, 1 pM: an experimental group treated with 1 pM of the peptide of the present disclosure after treatment with hydrogen peroxide, 50 pM: an experimental group treated with 50 pM of the peptide of the present disclosure after treatment with hydrogen peroxide, and 0.5 nM: an experimental group treated with 0.5 nM of the peptide of the present disclosure after treatment with hydrogen peroxide;

FIG. 4 depicts graphs showing cell proliferation rates of peptides (ML1-L2, ML1-K2, and ML1-R2) prepared by partially modifying sequences of the erythropoietin-derived ML1 peptide:

Control: non-treated cells as a control group,

Scr: cells treated with 1 pM of Scr peptide after treatment with hydrogen peroxide, as a negative control group, 1 pM: an experimental group treated with 1 pM of the peptide of the present disclosure, 50 pM: an experimental group treated with 50 pM of the peptide of the present disclosure, 0.5 nM: an experimental group treated with 0.5 nM of the peptide of the present disclosure, 0.5 IU/mL EPO: an experimental group treated with 0.5 IU/ml of natural erythropoietin, 1 IU/mL EPO: an experimental group treated with 1 IU/ml of natural erythropoietin, and 10 IU/mL EPO: an experimental group treated with 10 IU/ml of natural erythropoietin;

FIG. 5 depicts graphs showing cell proliferative effects of the erythropoietin-derived peptides and peptides prepared by partially modifying sequences thereof;

FIG. 6 shows an illustration of a structure of a complex of erythropoietin receptor (EPOR) and erythropoietin (EPO) of one embodiment and binding target sites; and FIG. 7 shows an illustration of a substitution process of amino acid sequences of one embodiment.

DESCRIPTION

An aspect provides a peptide, which is described by any one amino acid sequence selected from the group consisting of SEQ ID NOS: 1 to 25.

The peptide may be derived from an erythropoietin protein sequence. The peptide may bind to an erythropoietin receptor and may form an alpha-helical structure.

The peptide may exhibit cell protective activity and may have no side effect of cell proliferation.

The peptide of one embodiment may bind to a target site 1 or a target site 2 of an erythropoietin receptor.

The erythropoietin receptor (EPOR) has two target sites, through which EPOR forms a complex with erythropoietin (EPO). According to previous studies, of the two binding target sites, the target site 1 forms a strong bond (KD=~1 nM) and the target site 2 forms a weak bond (KD=~1 pM) (see FIG. 6).

The target site targeted in the present disclosure is a weak binding site, and the weak binding of EPOR and the peptide of the present disclosure may prevent the side effect (proliferative effect) which is induced by binding of natural EPO to EPOR thereof. Arg103, Ser104, Leu105, Leu108, and Arg110 are known as crucial amino acid sequences in EOPR, and based on EPO sequences directly binding to these sequences, the target site was determined.

In one embodiment, the present inventors synthesized peptides from a partial target site of natural EPO according to a known solid phase peptide synthesis technology, and specific characteristics of the respective peptides were identified (see Tables 1 and 2). Further, "LHVDKAVSGL-RSLTTL" (SEQ ID NO: 23), which is part of a basic sequence of ML1 was used to prepare peptides having modified amino acids at both ends thereof (see Table 7).

The present inventors confirmed that the peptides of the present disclosure may bind to EPOR to exert their actions (see FIG. 1, and Tables 8 and 9). The present inventors also confirmed that the erythropoietin-derived peptides prepared in the present disclosure may form a stable alpha-helix like natural EPO.

The present inventors confirmed that cells under stress environments induced by increased reactive oxygen species due to hydrogen peroxide may be protected by treatment with the erythropoietin-derived peptide prepared in the present disclosure (see FIGS. 2 and 3). The present inventors confirmed that inhibition of mitochondrial activity under stress environments induced by increased reactive oxygen species due to hydrogen peroxide may be suppressed by treatment with the erythropoietin-derived peptide prepared in the present disclosure (see FIG. 3). The present inventors confirmed that the peptides (ML1-L2, ML1-K2, and ML1-R2) prepared in the present disclosure have no side effect of cell proliferation (see FIG. 4).

Accordingly, the peptides of the present disclosure may bind to EPOR and may inhibit cell death without the side effect of cell proliferation, thereby being usefully applied as an EPO substitute to the prevention or treatment with neurodegenerative diseases.

Another aspect provides a pharmaceutical composition for preventing or treating a neurodegenerative disease, the pharmaceutical composition including, as an active ingredient, the peptide described by any one amino acid sequence selected from the group consisting of SEQ ID NOS: 1 to 25, one or more polynucleotides encoding the peptide, a vector including the polynucleotide, or a host cell including the vector.

The composition may exhibit cell protective activity and may have no side effect of cell proliferation.

The neurodegenerative disease may be selected from the group consisting of stroke, paralysis, myocardial infarction, dementia, Alzheimer's disease, Parkinson's disease, multiple sclerosis, Huntington's disease, Pick's disease, and Creutzfeldt-Jakob disease.

The host cell may be an HEK-293E cell, a Chinese hamster ovary (CHO) cell, a baby hamster kidney (BHK) cell, an NIH-3T3 cell, an HEK-293T cell, or a COS-7 cell.

The vector may be selected from the group consisting of a linear DNA vector, a plasmid DNA vector, or a recombinant viral vector. The recombinant virus may be selected from the group consisting of retroviruses, adenoviruses, adeno-associated viruses, herpes simplex viruses, and lentiviruses.

A therapeutically effective dose of the composition may vary depending on various factors, for example, an administration method, a target area, a patient's conditions, etc. Thus, when the composition is used in the human body, the administration dose is required to be suitably determined by taking into consideration both safety and efficiency. It is also possible to estimate the dose for human administration from the effective dose determined through an animal test. Such considerations to be taken into the determination of the effective dose are described, for example, in Hardman and Limbird, eds., Goodman and Gilman's The Pharmacological Basis of Therapeutics, 10th ed. (2001), Pergamon Press; and E. W. Martin ed., Remington's Pharmaceutical Sciences, 18th ed. (1990), Mack Publishing Co.

The composition may also include a carrier, a diluent, an excipient, or a combination of two or more thereof, which are commonly used in biological formulations. The pharmaceutically acceptable carrier is not particularly limited, as long as it is suitable for in vivo delivery of the composition. For example, the compounds described in Merck Index, 13th ed., Merck & Co. Inc., physiological saline, sterile water, Ringer's solution, buffered saline, a dextrose solution, a maltodextrin solution, glycerol, ethanol, and a mixture of one or more of these components may be used. If necessary, the composition may include other common additives such as antioxidants, buffers, bacteriostatic agents, etc.

In addition, the composition may be prepared into injectable formulations, such as aqueous solutions, suspensions, and emulsions, pills, capsules, granules, or tablets, by adding diluents, dispersing agents, surfactants, binders, and lubricants thereto. Furthermore, the composition may be appropriately formulated according to each disease or component by a suitable method known in the art or by using a method disclosed in Remington's Pharmaceutical Science (Mack Publishing Company, Easton Pa., 18th, 1990).

The composition may further include one or more active ingredients having identical or similar functions. The composition may include the protein in an amount of 0.0001% by weight to 10% by weight, or 0.001% by weight to 1% by weight, based on the total weight of the composition.

The composition may be administered parenterally (e.g., intravenous, subcutaneous, intraperitoneal, or topical application) or orally according to the intended method. The administration dose may vary depending on a patient's weight, age, sex, health conditions, diet, administration time, administration method, excretion rate, and severity of the disease. A daily dose of the composition may 0.0001 mg/ml to 10 mg/ml or 0.0001 mg/ml to 5 mg/ml, and the composition may be administered once or several times a day.

The vector including the polynucleotide encoding the peptide may be included in an amount of 0.05 mg to 500 mg or 0.1 mg to 300 mg, and the recombinant virus including the polynucleotide encoding the peptide of the present disclosure may be included in an amount of $10^3$ IU to $10^{12}$ IU ($10$ PFU to $10^{10}$ PFU) or $10^5$ IU to $10^{10}$ IU, but is not limited thereto.

Further, the cell including the polynucleotide encoding the peptide may be included in an amount of $10^3$ cells to $10^8$ cells, for example, $10^4$ cells to $10^8$ cells, $10^3$ cells to $10^7$ cells, or $10^4$ cells to $10^7$ cells.

With regard to the effective dose of the composition including the vector or cell including the polynucleotide encoding the peptide as an active ingredient, the vector may be administered in an amount of 0.05 mg/kg to 12.5 mg/kg, the recombinant virus may be administered in an amount of $10^7$ viral particles to $10^{11}$ viral particles ($10^5$ IU to $10^9$ IU)/kg, and the cell may be administered in an amount of $10^3$ cells/kg to $10^6$ cells/kg, or the vector may be administered in an amount of 0.1 mg/kg to 10 mg/kg, the recombinant virus may be administered in an amount of $10^8$ viral particles to $10^{10}$ viral particles ($10^6$ IU to $10^8$ IU)/kg, and the cell may be administered in an amount of $10^2$ cells/kg to $10^5$ cells/kg twice or three times a day. The composition is not particularly limited thereto, and may vary depending on a patient's conditions and development of the neurodegenerative disease.

The composition may further include a carrier, an excipient, and a diluent which are commonly used in the preparation of pharmaceutical compositions. The composition may be parenterally administered, and the parenteral administration may be selected from skin external application, intraperitoneal injection, intrarectal injection, subcutaneous injection, intravenous injection, intramuscular injection, and intrathoracic injection, but is not limited thereto.

The composition may be formulated in the form of an external preparation, a suppository, and a sterile injectable solution according to common methods, respectively. The carrier, the excipient, and the diluent which may be included in the composition may include lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate, and mineral oil. The formulation may be prepared using a commonly used diluent or excipient, such as a filler, an extender, a binder, a wetting agent, a disintegrant, a surfactant, etc. A formulation for parenteral administration may include a sterilized aqueous solution, a non-aqueous solvent, a suspension, an emulsion, a lyophilized formulation, and a suppository. The non-aqueous solvent formulation and the suspension formulation may be propylene glycol, polyethylene glycol, a vegetable oil such as olive oil, or injectable ester such as ethyloleate. A base for the suppository formulation may be witepsol, macrogol, tween 61, cacao butter, laurin butter, glycerogelatin, etc.

Still another aspect provides a method of preventing or treating a neurodegenerative disease, the method including administering the composition including, as an active ingredient, the peptide, one or more polynucleotides encoding the peptide, the vector including the polynucleotide, or the host cell including the vector.

An appropriate administration dose of the composition may vary depending on a patient's conditions and body weight, severity of the disease, a type of a drug, administration route and period, but may be appropriately selected by those skilled in the art. For better effects, the composition may be administered at a dose of 0.0001 mg/kg to 1 g/kg or 0.001 mg/kg to 200 mg/kg per day, but is not limited thereto. The administration may be performed once or several times a day. However, the administration dose does not limit the scope of the present disclosure in any aspect. Further, the therapeutic agent may be administered via various routes to mammals such as rats, mice, livestock, humans, etc. All modes of administration are contemplated, for example, administration may be made orally, rectally, or by intravenous, intramuscular, subcutaneous, intradural, or intracerebroventricular injection.

Still another aspect provides use of the composition including, as an active ingredient, the peptide, one or more polynucleotides encoding the peptide, the vector including the polynucleotide, or the host cell including the vector in the preparation of a prophylactic or therapeutic agent for a neurodegenerative disease.

The peptide of the present disclosure may bind to EPOR and may inhibit cell death without the side effect of cell proliferation, thereby being usefully applied as an EPO substitute to the prevention or treatment of a neurodegenerative disease.

Advantageous Effects of Disclosure

A peptide according to an aspect has a simple structure, as compared with natural human erythropoietin, and thus the peptide easily passes through a tissue-blood barrier, exhibits excellent physiological activity due to cell protective effects, and is economically advantageous due to its low production cost. Further, the peptide has no side effects of cell proliferation, and thus a pharmaceutical composition including the described erythropoietin-derived peptide of an aspect as an active ingredient may be usefully applied to the prevention or treatment of cell damage-related illnesses, such as stroke, mechanical damage or ischemic injury to the nervous system, myocardial infarction, retinal damage, diabetes, etc., and the prevention of cell damages.

EXAMPLES

Hereinafter, exemplary embodiments will be provided for better understanding of the present disclosure. However, the following exemplary embodiments are provided only for understanding the present disclosure more easily, but the content of the present disclosure is not limited thereby.

Example 1. Synthesis of Erythropoietin-Derived Peptides

Erythropoietin-derived peptides of the present disclosure were synthesized as monomers according to a known solid phase peptide synthesis technology (Peptron, Daejeon, Korea).

In detail, erythropoietin-derived peptides, which are able to bind to crucial amino acid sequences (Arg103, Ser104, Leu105, Leu108 and Arg110) in a sequence of a target site (site 2) of the natural erythropoietin receptor were synthesized, and specific characteristics of the peptides were examined, respectively. To determine concentrations of the synthesized peptides, liquid chromatography/mass-selective detector (HP 1100 series) was used. Purity was measured by high performance liquid chromatography (SHIMADZU prominence HPLC) (>95% purity). The erythropoietin-derived peptides are shown in Table 1 below.

TABLE 1

| Peptide name | Sequence | SEQ ID NO: |
|---|---|---|
| ML1 | LQLHVDKAVSGLRSLTTLLRALG | 1 |
| ML2 | LHVDKAVSGLRSLTTLLRAL | 2 |
| ML3 | TKVNFYAWKR | 3 |
| ML4 | DKAVSGLRSLTTLLRALGAQKEAI | 4 |
| ML5 | SGLRSLTTLLRALG | 5 |
| ML6 | SGLRSLTTLLRALGAQKEAI | 6 |
| ML7 | WEPLQLHVDKAVSGLRSLTTLLRAL | 7 |
| ML8 | DKAVSGLRSLTTLLRAL | 8 |
| ML1-1 | LQLHVLKRVSGLLSHTMLLKALG | 9 |
| ML2-1 | RHVQKAESGLRSLTKLLREL | 10 |
| ML3-1 | TRVNYQAWKR | 11 |

TABLE 1-continued

| Peptide name | Sequence | SEQ ID NO: |
|---|---|---|
| ML4-1 | KKAVSGLKTLTHILRALGAQKEAI | 12 |
| ML5-1 | AGLRSRAHLRRALA | 13 |
| ML6-1 | KGLRSLISLLRALGAQKEAI | 14 |
| ML7-1 | DEALDLEVDKAATGLRTLTTLIRAL | 15 |
| ML8-1 | NKAVAGLRSLTVN | 16 |

Hydrophobicity, charge, and isoelectric point (pi) of the erythropoietin-derived peptides, ML1-1, ML2-1, ML3-1, ML4-1, ML5-1, ML6-1, ML7-1, and ML8-1 were calculated and shown in Table 2 below.

TABLE 2

| Peptide name | Hydrophobicity | Charge(pH 7) | pI | Target site |
|---|---|---|---|---|
| ML1-1 | 8.25 | 3.4 | 11.2 | 2 |
| ML2-1 | −4.45 | 3.2 | 10.94 | 2 |
| ML3-1 | −10.07 | 2.9 | 10.94 | 1 |
| ML4-1 | 5 | 6.1 | 11.41 | 2 |
| ML5-1 | −4.15 | 4.1 | 12.48 | 2 |
| ML6-1 | 8.85 | 2.9 | 10.94 | 2 |
| ML7-1 | 2.05 | −2.1 | 4.59 | 2 |
| ML8-1 | 5.7 | 1.9 | 11.12 | 2 |

Example 2. Synthesis of Erythropoietin-Derived Peptides Using Partial Sequence (1)

For sequence modification experiments, a binding model of erythropoietin and its receptor was based on a previously known binding structure (Protein Data Bank ID: 1 EER). Based on known characteristics of amino acids, amino acids of the erythropoietin-derived peptides were substituted. Amino acids are classified into 4 types (① non-polar or hydrophobic, ② neutral, ③ negatively charged, ④ positively charged) according to polarity of their side chains. Based on information of non-polar (hydrophobic), neutral, negatively charged, or positively charged amino acids, the existing amino acid sequences were substituted to induce modification in respective characteristics.

Peptides prepared by partially modifying sequences of ML1 peptide and their characteristics are shown in Tables 3 and 4.

TABLE 3

| Peptide name | Sequence | SEQ ID NO: |
|---|---|---|
| ML1 | LQLHVDKAVSGLRSLTTLLRALG | 1 |
| ML1-H1 | LQLHVLKAVSGLLTHTTLLKALG | 17 |
| ML1-H2 | LQLHVLKAVSGLLTLTMIRRALG | 18 |
| ML1-H3 | LQLHVLKAVAGLRTLAMIRRALA | 19 |

TABLE 4

| Peptide name | Number of residue | Molecular weight | Absorption coefficient | Isoelectric point | Net charge (pH 7) | Predicted solubility |
|---|---|---|---|---|---|---|
| ML1 | 23 | 2461.9 g/mol | 0 $M^{-1}cm^{-1}$ | pH 11.23 | 2.1 | Low solubility in water |
| ML1-H1 | 23 | 2426.94 g/mol | 0 $M^{-1}cm^{-1}$ | pH 10.73 | 2.2 | Low solubility in water |
| ML1-H2 | 23 | 2504.09 g/mol | 0 $M^{-1}cm^{-1}$ | pH 12.13 | 3.1 | Low solubility in water |
| ML1-H3 | 23 | 2515.12 g/mol | 0 $M^{-1}cm^{-1}$ | pH 12.41 | 4.1 | Low solubility in water |

Example 3. Synthesis of Erythropoietin-Derived Peptides Using Partial Sequence (2)

Partial sequences of the peptides were substituted using the basic sequence of ML1 as in Example 2. In this regard, amino acids were substituted based on the existing binding model of erythropoietin and its receptor without hindering the existing binding structure (a distance between proteins or a protein structure). FIG. 7 illustrates exemplary substitution of amino acid sequences. Since substitution of alanine (Ala) with arginine (Arg) hinders the existing binding, substitution with serine (Ser) may be performed to prevent hindrance of the binding.

Peptides prepared by modifying the charge of the ML1 peptide and characteristics thereof are shown in Tables 5 and 6 below.

TABLE 5

| Peptide name | Sequence | SEQ ID NO: |
|---|---|---|
| ML1-C1 | LDLEVDKAVSGLRSLTTLLRALG | 20 |
| ML1 | LQLHVDKAVSGLRSLTTLLRALG | 1 |
| ML1-C2 | LQRHVDKRVSGLRSLTTLLRALG | 21 |
| ML1-C3 | LQRHVKKRVKGLKSLTTLLRALG | 22 |

TABLE 6

| Peptide name | Number of residue | Molecular weight | Absorption coefficient | Isoelectric point | Net charge (pH 7) | Predicted solubility |
|---|---|---|---|---|---|---|
| ML1-C1 | 23 | 2440.83 g/mol | 0 $M^{-1}cm^{-1}$ | pH 6.96 | 0 | High solubility in water |
| ML1 | 23 | 2461.9 g/mol | 0 $M^{-1}cm^{-1}$ | pH 11.23 | 2.1 | Low solubility in water |
| ML1-C2 | 23 | 2590.04 g/mol | 0 $M^{-1}cm^{-1}$ | pH 12.12 | 4.1 | High solubility in water |
| ML1-C3 | 23 | 2616.21 g/mol | 0 $M^{-1}cm^{-1}$ | pH 12.45 | 7.1 | High solubility in water |

Example 4. Synthesis of Erythropoietin-Derived Peptides Using Partial Sequence (3)

A partial sequence "LHVDKAVSGLRSLTTL" (SEQ ID NO: 23) of the ML1 basic sequence was used to prepare peptides having modified amino acids at both ends thereof, as in Table 7 below.

TABLE 7

| Peptide name | Sequence | SEQ ID NO: |
|---|---|---|
| ML1-L2 | L HVDKAVSGLRSLTT L | 23 |
| ML1-K2 | K HVDKAVSGLRSLTT K | 24 |
| ML1-R2 | R HVDKAVSGLRSLTT R | 25 |

Experimental Example

I. Determination of Binding Affinity of Erythropoietin-Derived Peptide to Erythropoietin Receptor (EPOR)

To determine whether the erythropoietin-derived peptides prepared in Examples 1 to 3 are able to bind to the erythropoietin receptor having the target site to exert their actions, a surface plasmon resonance (SPR) technique was used to determine binding affinity. The SPR technique is to measure interactions between biomolecules in real-time by using an optical principle without specific labeling, and is a system analyzing affinity between two molecules and kinetics, i.e., an association rate (Ka) and a dissociation rate (Kd).

In detail, real-time SPR analysis may be performed using Reichert SPR Biosensor SR 7500C instrument (Reichert Inc., NY, USA). Soluble mouse EPOR chimera proteins (R&D Systems, Minneapolis, Minn., USA) were covalently linked to a carboxymethylated dextran matrix-coated chip (BR-1005-39, Pharmacia Biosensor AB) by an amine coupling procedure using an amine coupling kit (BR-1000-50, GE Healthcare, USA) in accordance with manufacturer's instructions. Each 5 pM, 2.5 pM, and 1.25 pM of the peptide samples of the present disclosure and scrambled peptides were applied at a flow rate of 5 μl/minute, and the experiments were independently performed in duplicate. For signal normalization, DMSO was applied at a flow rate of 5 μl/minute. After each binding cycle, the sensor chip was regenerated by injecting 25 mM of acetic acid at a flow rate of 20 μl/minute.

As a result, as shown in FIG. 1, the result values were increased according to the concentrations of the erythropoietin-derived peptides of one embodiment, and thus it was confirmed that the erythropoietin-derived peptides bind to the erythropoietin receptor having the target site to exert their actions (FIG. 1). Further, as shown in Tables 8 and 9, it was also confirmed that the erythropoietin-derived peptides of one embodiment exhibited binding affinities similar to the known binding affinity (~1 uM).

TABLE 8

| | Ka | Kd | KD |
|---|---|---|---|
| ML1 | $1.311 \times 10^3$ | $8.5 \times 10^{-3}$ | 6.46077 μM |
| ML2 | $1.6 \times 10$ | $4.4 \times 10^{-3}$ | 273 μM |
| ML3 | $2.05 \times 10^2$ | $3 \times 10^{-3}$ | 14.6341 μM |
| ML4 | $2.2 \times 10^2$ | $2.2 \times 10^{-3}$ | 10 μM |
| ML5 | $3.04 \times 10^2$ | $0.1 \times 10^{-3}$ | 0.32894 μM |
| ML6 | $5.0 \times 10$ | $4.5 \times 10^{-2}$ | 900 μM |
| ML7 | $3.00 \times 10^2$ | $0.2 \times 10^{-2}$ | 6.666 μM |
| ML8 | $1.8 \times 10^2$ | $0.8 \times 10^{-1}$ | 444.44 μM |
| ML1-1 | $5.55 \times 10^3$ | $5.9 \times 10^{-3}$ | 1.06 μM |
| ML2-1 | $3.1 \times 10^2$ | $4.1 \times 10^{-3}$ | 14.3 μM |
| ML3-1 | $3.08 \times 10^3$ | $1.3 \times 10^{-2}$ | 4.31 μM |
| ML4-1 | $4.10 \times 10^2$ | $1.20 \times 10^{-2}$ | 39.34 mM |
| ML5-1 | $4.42 \times 10^2$ | $3.46 \times 10^{-2}$ | 78.28 μM |
| ML6-1 | $1.9 \times 10^2$ | $3 \times 10^{-2}$ | 157.8 μM |
| ML7-1 | $2.26 \times 10^2$ | $1.44 \times 10^{-2}$ | 63.70 μM |
| ML8-1 | $6.4 \times 10$ | $1.5 \times 10^{-1}$ | 2.37 mM |

TABLE 9

| | Km | Ka | Kd | KD |
|---|---|---|---|---|
| ML1 | 1.26E+05 | 1310.8 | 8.47E−03 | 6.46077 μM |
| ML1-H1 | 4.79E+05 | 1.01E+03 | 7.94E−03 | 7.84542 μM |
| ML1-H2 | 1.00E+10 | 3434.3 | 1.05E−03 | 306.977 nM |
| ML1-H3 | 1.00E+10 | 4157.6 | 4.77E−03 | 1.14651 μM |
| ML1-C1 | 9.23E+05 | 1745.7 | 0.2617 | 149.921 μM |
| ML1-C2 | 4.58E+05 | 1.59E+03 | 0.01876 | 11.7609 μM |
| ML1-C3 | 1.46E+05 | 1104.9 | 0.01086 | 9.82836 μM |

In other words, it was confirmed that the peptides according to specific embodiments are those derived from the erythropoietin binding site, and thus they have binding affinity to the erythropoietin receptor.

Determination of secondary alpha-helix formation of erythropoietin-derived peptide The present inventors determined whether the erythropoietin-derived peptides synthesized in Example 1 are able to form a stable alpha-helix, like natural erythropoietin.

As a result, it was confirmed that the erythropoietin-derived peptides synthesized in Example 1 formed a stable secondary alpha-helix, like natural erythropoietin.

II. Determination of Cell Protective Effect of Erythropoietin-Derived Peptide (1)

To determine whether the erythropoietin-derived peptides prepared in Examples 1 to 3 exhibit cell protective effects, cell viability was determined under stress conditions where an increase in reactive oxygen species was induced by hydrogen peroxide ($H_2O_2$).

In detail, to evaluate cell viability, an MTS assay (CellTiter 96 Aqueous One Solution Cell Proliferation Assay, Promega, Madison, Wis., USA) was performed. PC12 cells were seeded in a 96-well plate (5×10⁴ cells per well), and an increase in reactive oxygen species was induced using 150 pM of hydrogen peroxide ($H_2O_2$). Thereafter, 25 ng/ml of nerve growth factor (NGF) was added as a positive control group, and 1 IU/ml of the erythropoietin compound, 0.25 pM, 1 pM, 2 pM, or 4 pM of the peptide of Example 1, each 0.25 pM, 1 pM, 2 pM, 10 pM, or 100 pM of the peptides of Example 2 and 3, or 0.1 pM, 1 pM, 50 pM, or 0.5 nM of the peptide of Example 4 was added, and 20 µl of an MTS solution was added to each well, and left for 3 hours. The initial number of cells (0 hour) and the number of cells after 48 hours were counted. Intracellular soluble formazan produced by cell reduction was determined by recording absorbance of each 96-well plate at a wavelength of 490 nm using a VERSA MAX.

As a result, as shown in FIG. 2, it was confirmed that the erythropoietin-derived peptides protected cells from cell death caused by the increase in reactive oxygen species (FIG. 2). This result was similar to the cell protective effect by treatment with the natural erythropoietin compound.

III. Determination of Cell Protective Effect of Erythropoietin-Derived Peptide (2)

To determine whether the erythropoietin-derived peptide prepared in Example 4 exhibits the cell protective effect, mitochondrial activity was determined under stress conditions where an increase in reactive oxygen species was induced by hydrogen peroxide ($H_2O_2$).

In detail, PC12 cells or human SH-SY5Y cells were seeded in a 96-well plate (5×10⁴ cells per well), and an increase in reactive oxygen species was induced using 150 pM of hydrogen peroxide ($H_2O_2$). Thereafter, 25 ng/ml of NGF was added as a positive control group, 1 IU/ml of the erythropoietin compound, or 0.1 pM, 1 pM, 50 pM, or 0.5 nM of the peptide of Example 4 were added.

When mitochondrial activity is suppressed, mitochondrial swelling due to abnormalities of the mitochondrial membrane potential, dysfunction due to oxidative stress such as reactive oxygen species or free radicals, dysfunction due to genetic factors, and dysfunction due to defects in oxidative phosphorylation for mitochondrial energy production occur. Thus, mitochondrial activity may be determined by measuring the mitochondrial membrane potential. Tetramethylrhodamine methyl ester (TMRM) staining of mitochondria was performed. Since TMRM staining intensity is increased in proportion to the mitochondrial membrane potential, the intracellular mitochondrial membrane potential was determined by measuring the TMRM staining intensity using a microplate reader (excitation, 485 nm; emission, 535 nm).

As a result, as shown in FIG. 3, it was confirmed that the erythropoietin-derived peptides suppressed inhibition of mitochondrial activity caused by increased reactive oxygen species (FIG. 3). This result was similar to the effect by treatment with the natural erythropoietin compound.

IV. Determination of Cell Proliferation-Inhibitory Effect of Erythropoietin-Derived Peptide (1)

Side effects such as cell proliferation were determined for the three peptides (ML1-L2, ML1-K2, and ML1-R2) prepared in Example 4.

In detail, to determine cell proliferation degree, an MTS assay (CellTiter 96 Aqueous One Solution Cell Proliferation Assay, Promega, Madison, Wis., USA) was performed. PC12 cells were seeded in a 96-well plate (5×10⁴ cells per well), and 1 pM of scrambled peptide (Scr) as a negative control group, 0.5 IU/ml, 1 IU/ml, or 10 IU/ml of the erythropoietin compound, or 1 pM, 10 pM, or 0.5 nM of the peptide of Example 4 was added, and 20 µl of an MTS solution was added to each well, and left for 3 hours. The initial number of cells (0 hour) and the number of cells after 48 hours were counted. Intracellular soluble formazan produced by cell reduction was determined by recording absorbance of each 96-well plate at a wavelength of 490 nm using a VERSA MAX.

As a result, as shown in FIG. 4, it was confirmed that all the peptides showed cell proliferation rates similar to that of the control group, and they showed no side effect of cell proliferation.

V. Determination of Cell Proliferation-Inhibitory Effect of Erythropoietin-Derived Peptide (2)

To determine the side effect of cell proliferation with respect to the peptides prepared in Examples 1 to 3, cell viability was evaluated by an MTT assay.

In detail, PC12 cells were cultured in a DMEM (Dulbecco's Modified Eagle's Medium) medium (Hyclone, USA) and an RPMI1640 medium (Hyclone, Utah, USA) each supplemented with 10% fetal bovine serum (FBS, Hyclone, Utah, USA), 100 unit/ml penicillin, and 100 µg/ml streptomycin (Hyclone, Utah, USA) in an incubator under conditions of 5% $CO_2$ and 37° C. PC12 cells were seeded in a 96-well culture plate at a density of 5×10⁴ cells/ml, and cultured under conditions of 37° C. and 5% $CO_2$ for 24 hours. Thereafter, the cells were treated with each of the peptides of Examples 1 to 3, which were prepared at a concentration of 10 ng/ml, followed by incubation for 24 hours. Thereafter, 20 µl of 5 mg/ml 3-[4,5-dimethyl-thiazol]-2,5-diphenyl-tetrazolium bromide (MTT) reagent was added thereto, and allowed to react for 2 hours. After reaction, 200 µl of dimethyl sulfoxide (DMSO, Duksan, Gyeonggi-do, Korea) was added thereto to completely dissolve formed formazan, and absorbance at 570 nm was measured using a microplate reader (Molecular Devices, CA, USA).

As a result, as shown in FIG. 5, it was confirmed that all the peptides showed cell proliferation rates similar to that of the control group, and they showed no side effect of cell proliferation.

The foregoing description of the present disclosure is for illustrative purposes only, and those of ordinary skill in the art readily understand that the present disclosure may be implemented in a different specific form without changing the technical spirit or essential characteristics thereof. It is therefore to be understood that the above-described embodiments are not limitative, but illustrative in all aspects.

The invention claimed is:

1. A peptide comprising the amino acid sequence of SEQ ID NO: 24 or 25.

2. The peptide of claim 1, wherein the peptide binds to an erythropoietin receptor.

3. The peptide of claim 1, wherein the peptide forms an alpha-helical structure.

4. The peptide of claim 1, wherein the peptide exhibits cell protective activity against oxidative damage induced by reactive oxygen species or $H_2O_2$.

5. The peptide of claim 1, wherein the peptide has no side effects of cell proliferation induced by binding of a natural erythropoietin to the erythropoietin receptor.

6. A pharmaceutical composition comprising the peptide of claim 1.

7. A method for protecting cells from oxidative damage induced by reactive oxygen species, comprising:

i) culturing and treating the cells with $H_2O_2$;

ii) administering the composition of claim 6 to the cells of step i) in vitro, thereby protecting the cells of step i) from oxidative damage induced by increased reactive oxygen species due to $H_2O_2$, wherein the protection of the cells against the oxidative damage is determined by detecting suppression of inhibition of mitochondrial activity caused by increased reactive oxygen species induced by H2O2 in the cells of step ii) as compared to the cells of step i).

* * * * *